(12) United States Patent
Nelson et al.

(10) Patent No.: US 9,562,834 B2
(45) Date of Patent: Feb. 7, 2017

(54) AQUEOUS COMPOSITIONS AND METHODS OF USING THE SAME FOR HISTOPATHOLOGICAL EVALUATION OF TISSUE SAMPLES

(71) Applicants: John J. Nelson, Biloxi, MS (US); Retha Edwards, Biloxi, MS (US)

(72) Inventors: John J. Nelson, Biloxi, MS (US); Retha Edwards, Biloxi, MS (US)

(*) Notice: Subject to any disclaimer, the term of this patent is extended or adjusted under 35 U.S.C. 154(b) by 23 days.

(21) Appl. No.: 14/695,769

(22) Filed: Apr. 24, 2015

(65) Prior Publication Data

US 2016/0054206 A1    Feb. 25, 2016

Related U.S. Application Data

(60) Provisional application No. 62/040,292, filed on Aug. 21, 2014.

(51) Int. Cl.
*G01N 1/30* (2006.01)

(52) U.S. Cl.
CPC .......... *G01N 1/30* (2013.01); *G01N 2001/307* (2013.01)

(58) Field of Classification Search
None
See application file for complete search history.

(56) References Cited

U.S. PATENT DOCUMENTS

| | | | |
|---|---|---|---|
| 3,329,572 A | 7/1967 | Malgouzou | |
| 3,864,272 A * | 2/1975 | Toma | C11D 9/225 510/147 |
| 5,298,222 A | 3/1994 | O'Leary | |
| 5,460,962 A | 10/1995 | Kemp | |
| 5,529,714 A * | 6/1996 | Tokosh | C11D 9/007 510/147 |
| 5,545,347 A | 8/1996 | Ouyang et al. | |
| 5,932,529 A | 8/1999 | Storey | |
| 6,893,653 B2 | 5/2005 | Abraham et al. | |
| 2003/0118540 A1 | 6/2003 | Charlton et al. | |
| 2008/0010754 A1 * | 1/2008 | Bureiko | A61K 8/042 8/406 |

FOREIGN PATENT DOCUMENTS

| | | |
|---|---|---|
| WO | 93/06204 | 4/1993 |
| WO | 2004/104152 | 12/2004 |
| WO | 2012/138829 | 10/2012 |
| WO | 2014/116997 | 7/2014 |

OTHER PUBLICATIONS

ACCORD, Laundry Detergent Ingredients Information Sheet, (2011).*
Google Date Stamp for ACCORD reference (last visited Sep. 24, 2015).*
International Search Report and the Written Opinion issued Nov. 30, 2015, in Application No. PCT/US15/46274.

* cited by examiner

*Primary Examiner* — Suzanne M Noakes
*Assistant Examiner* — Stephen Chong
(74) *Attorney, Agent, or Firm* — Oblon, McClelland, Maier & Neustadt, L.L.P.

(57) ABSTRACT

Aqueous solutions that include: (A) an organic polyol having from 2 to 20 carbon atoms and having a flash point of at least 93° C.; (B) a base; (C) a surfactant; and (D) water, where the aqueous solution does not include an organic solvent having a flash point below 23° C. and a boiling point of at least 38° C.

19 Claims, 39 Drawing Sheets
(39 of 39 Drawing Sheet(s) Filed in Color)

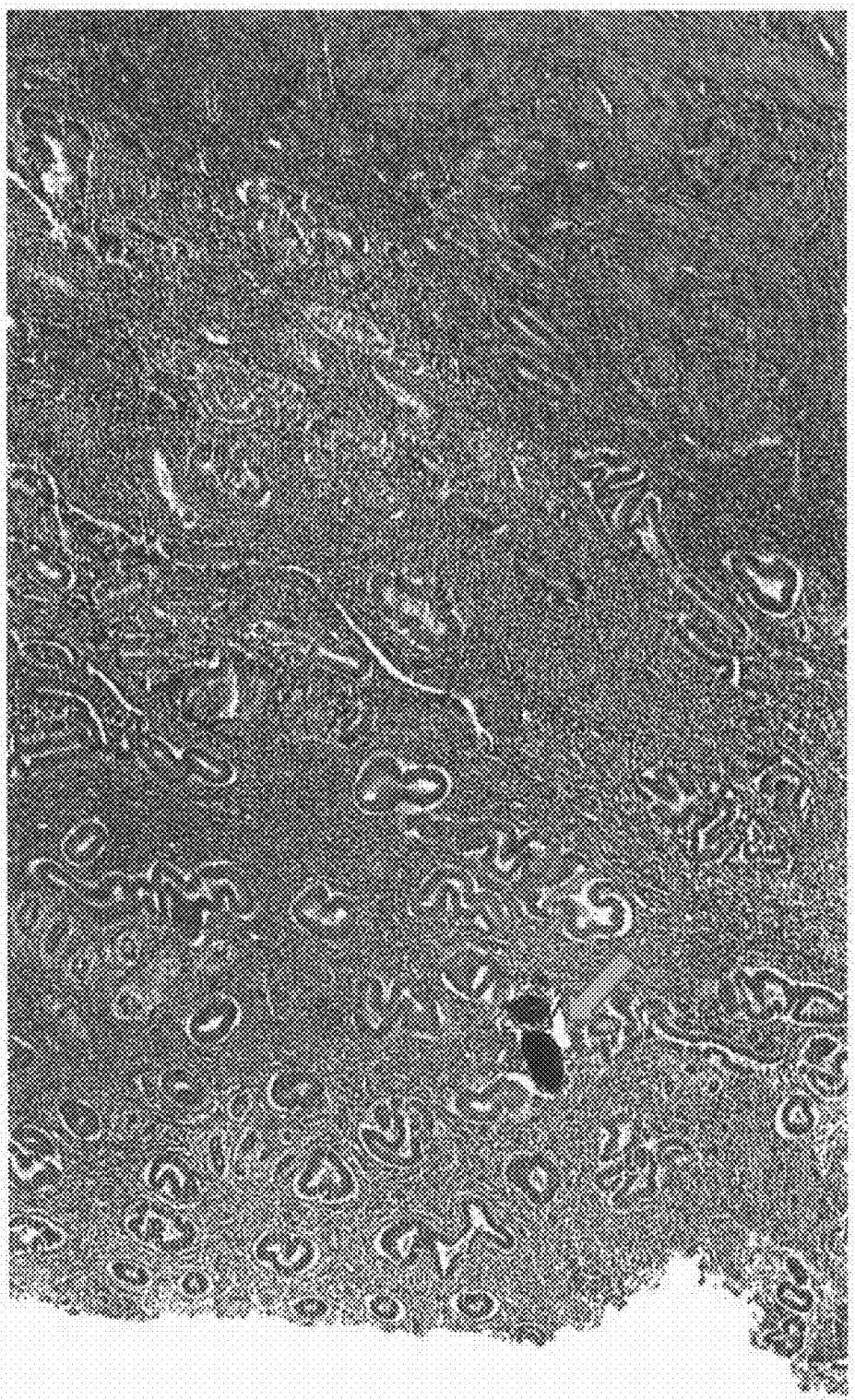
Fig 1: Without Product, Endometrium – LP (40X)

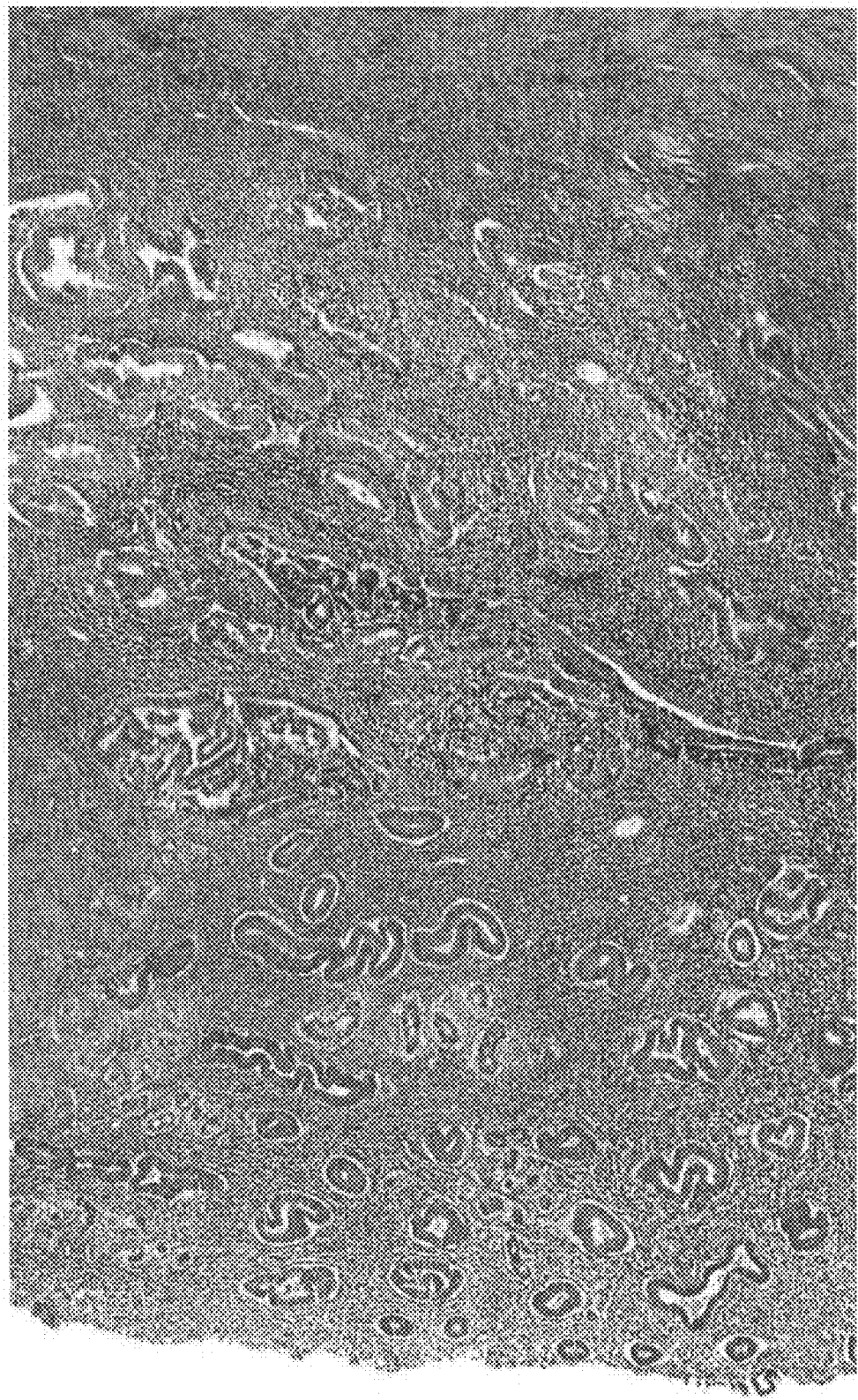
Fig. 2: With Product, Endometrium – LP (40X)

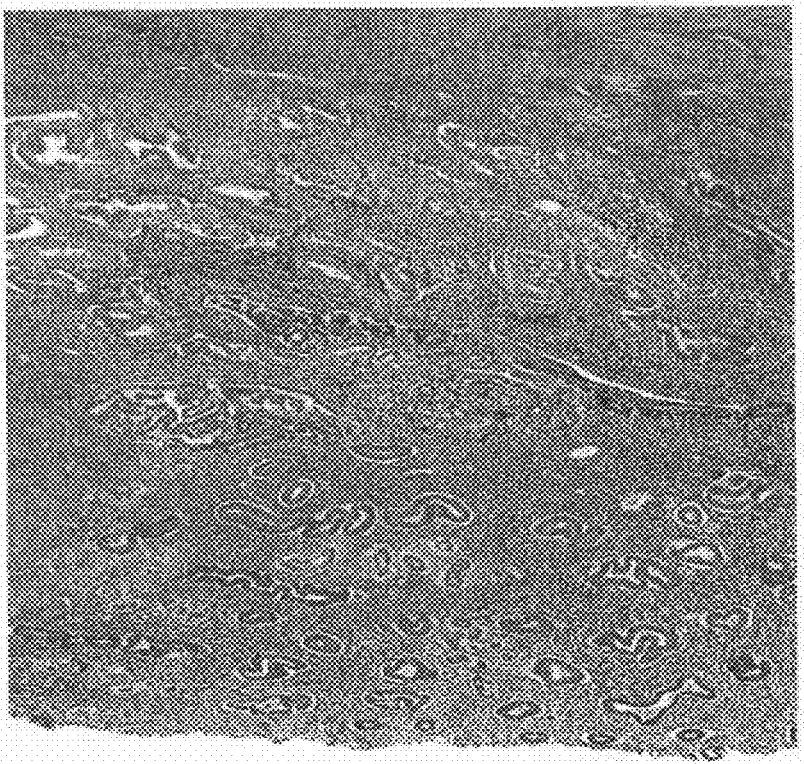
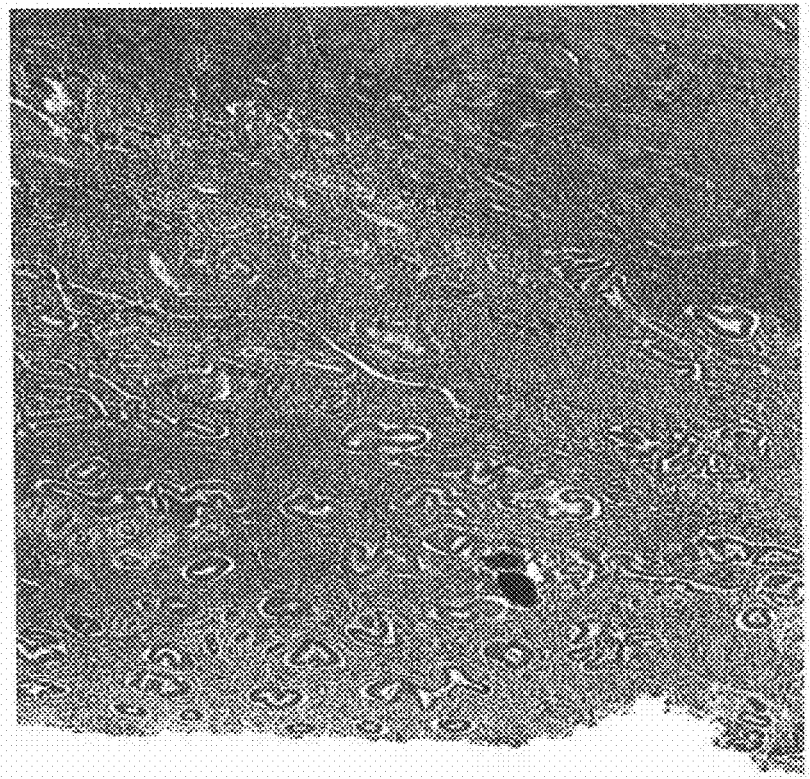
Fig. 3: Endometrium Comparison – Low Power (40X)
With Product (40X)
Without Product (40X)

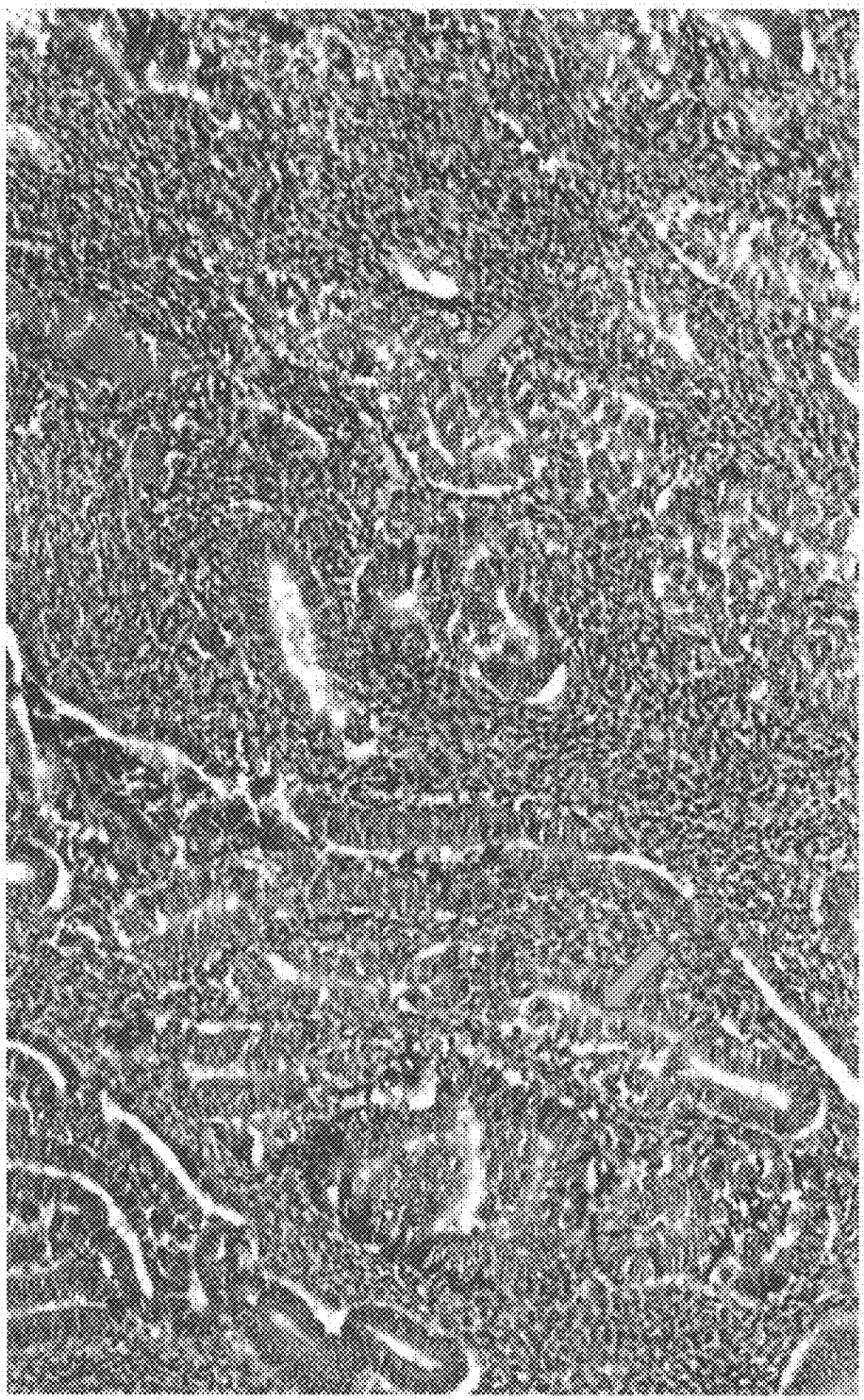
Fig. 4: Without Product, Endometrium – MP (100X)

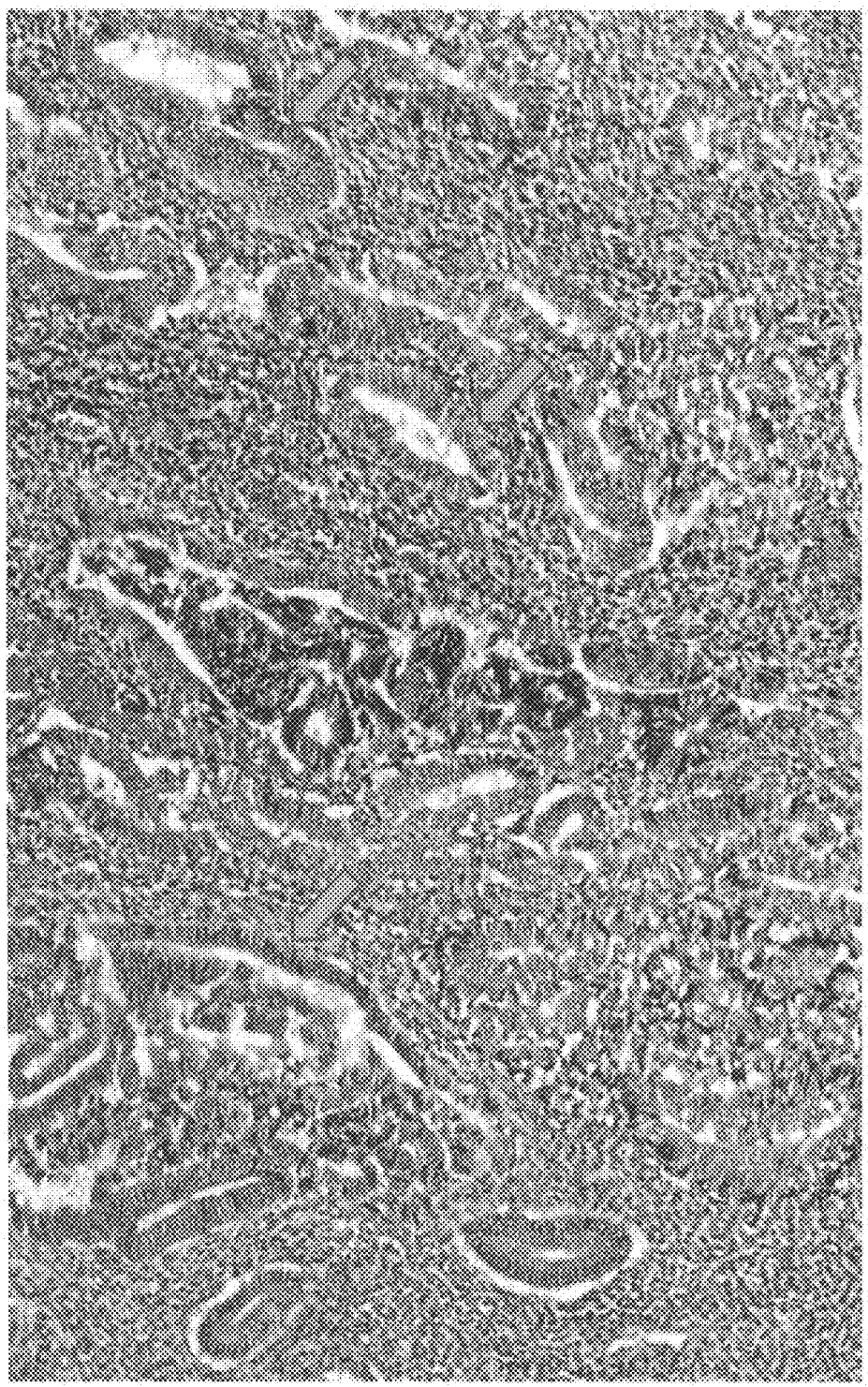
Fig. 5: With Product, Endometrium – MP (100X)

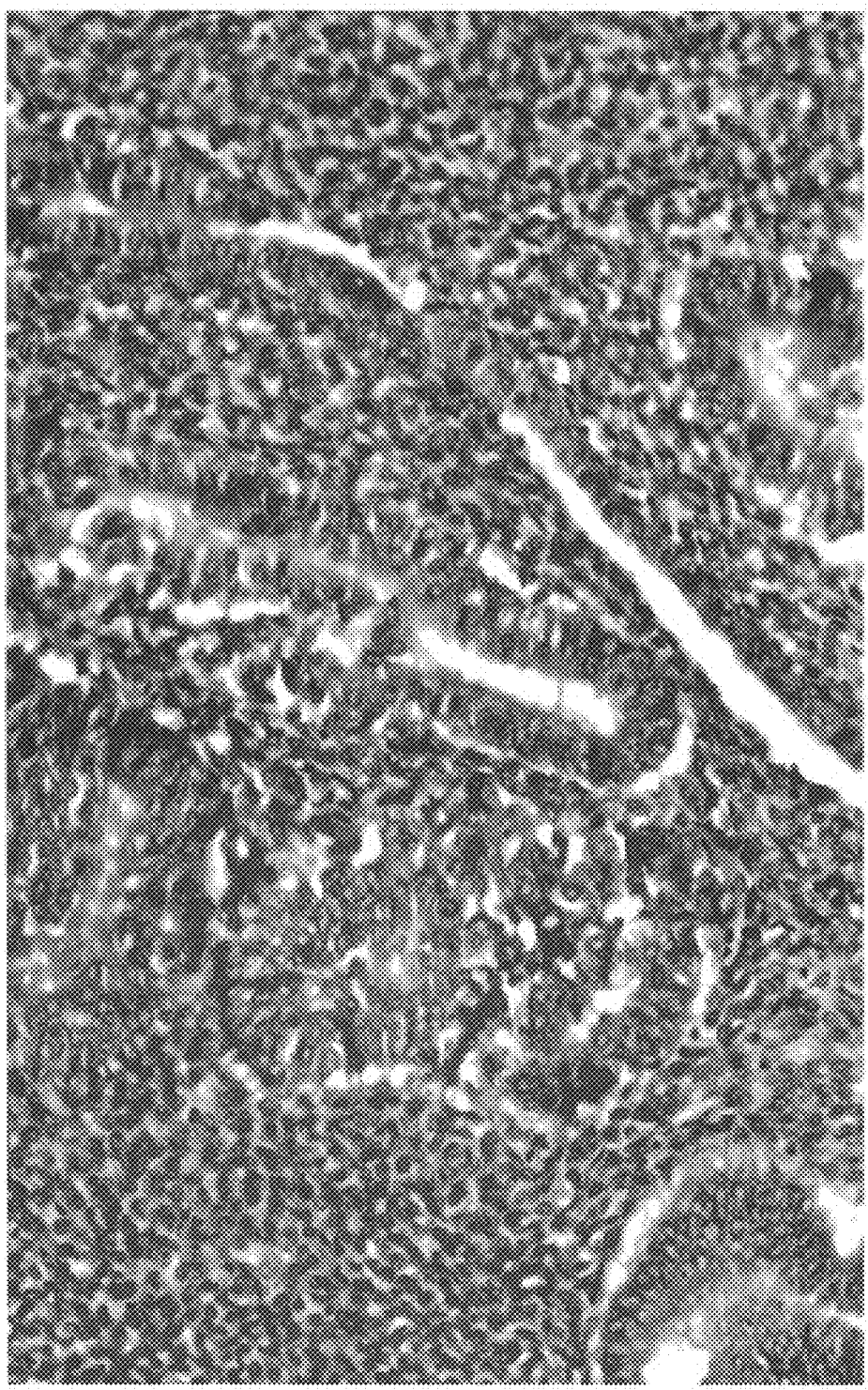
Fig. 6: Without Product, Endometrium – HP (400X)

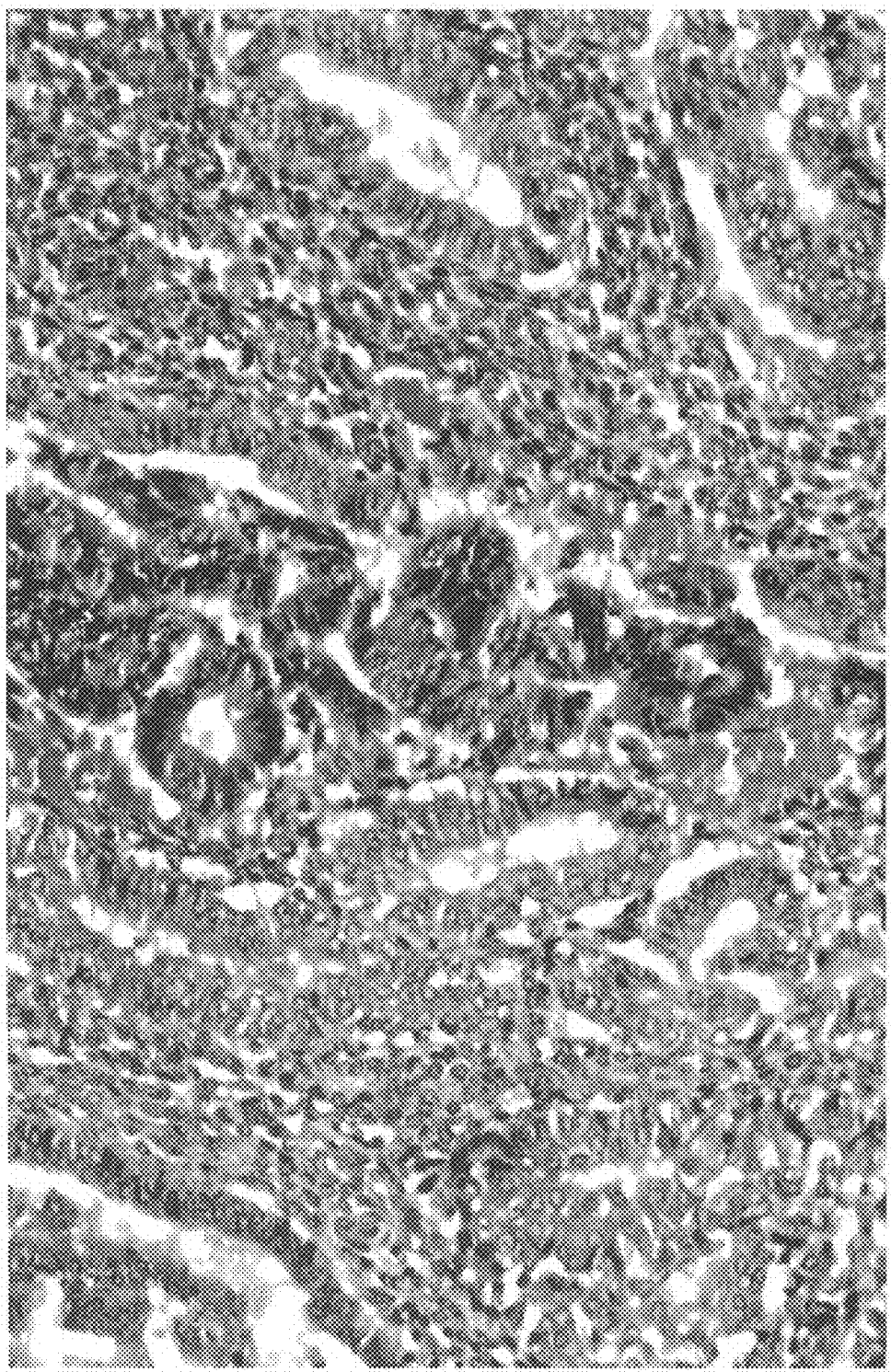

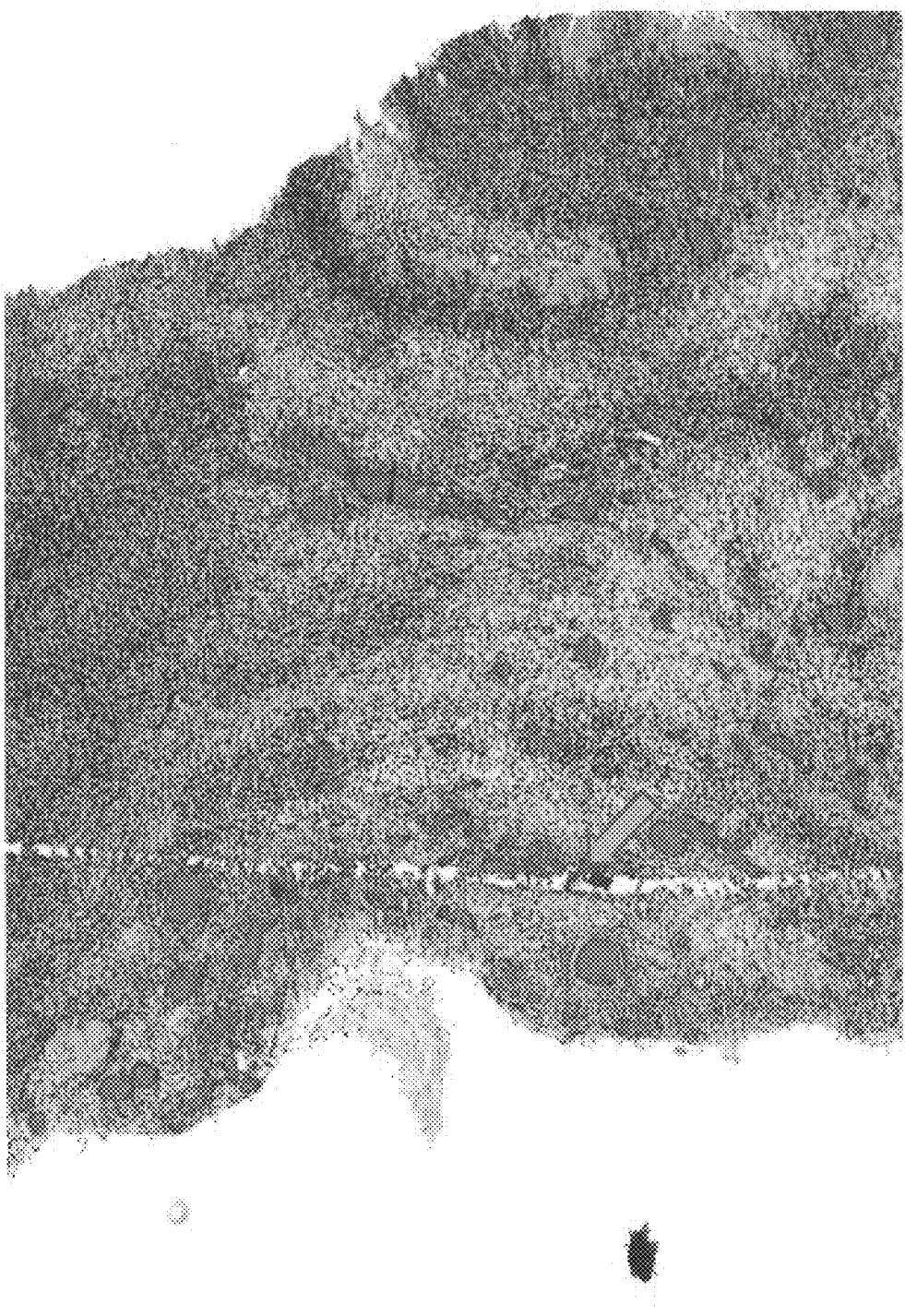
Fig. 8: Without Product, Myometrium – LP (40X)

Fig. 9: With Product, Myometrium – LP (40X)

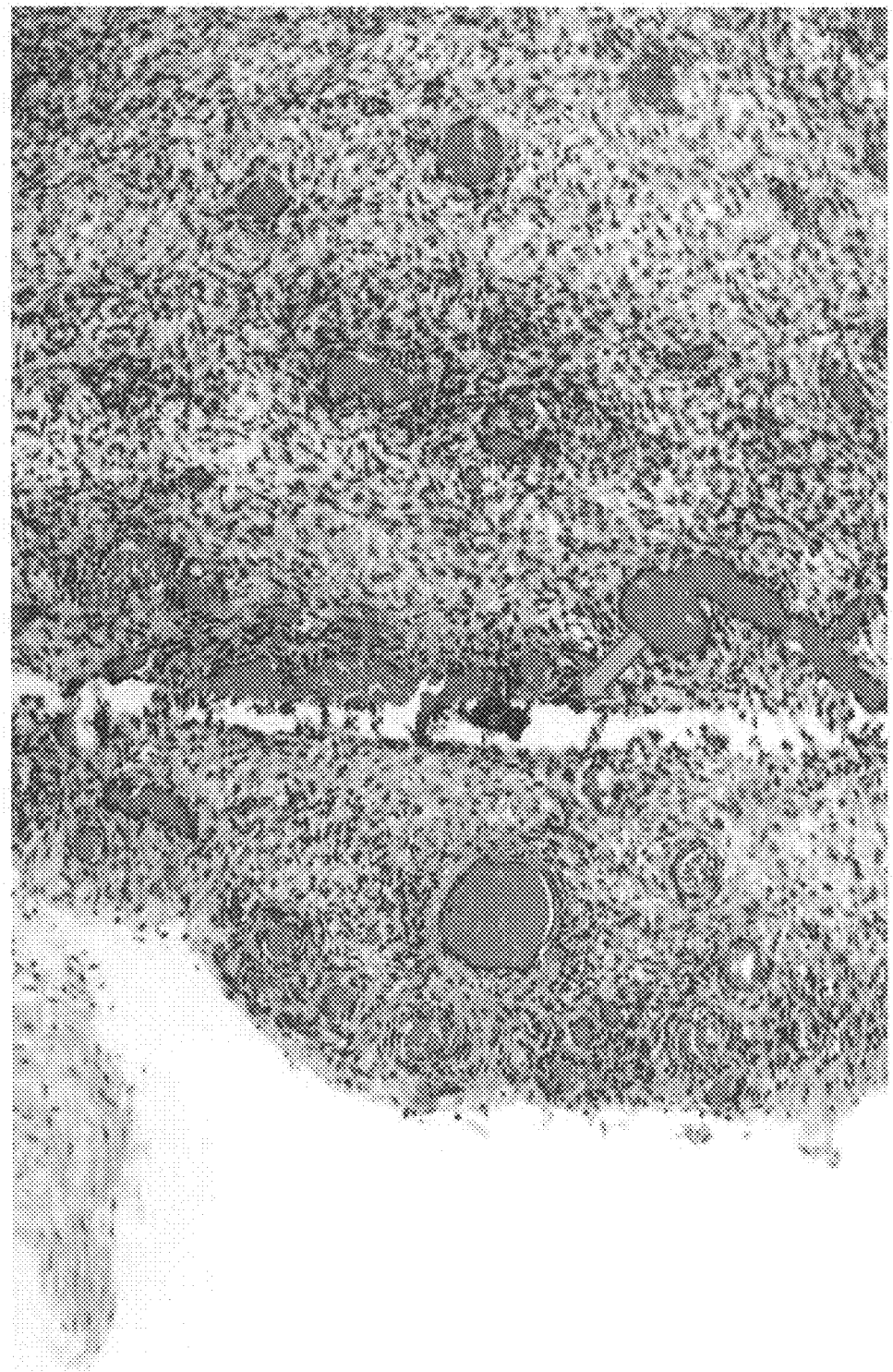
Fig. 10: Without Product, Myometrium – MP (100X)

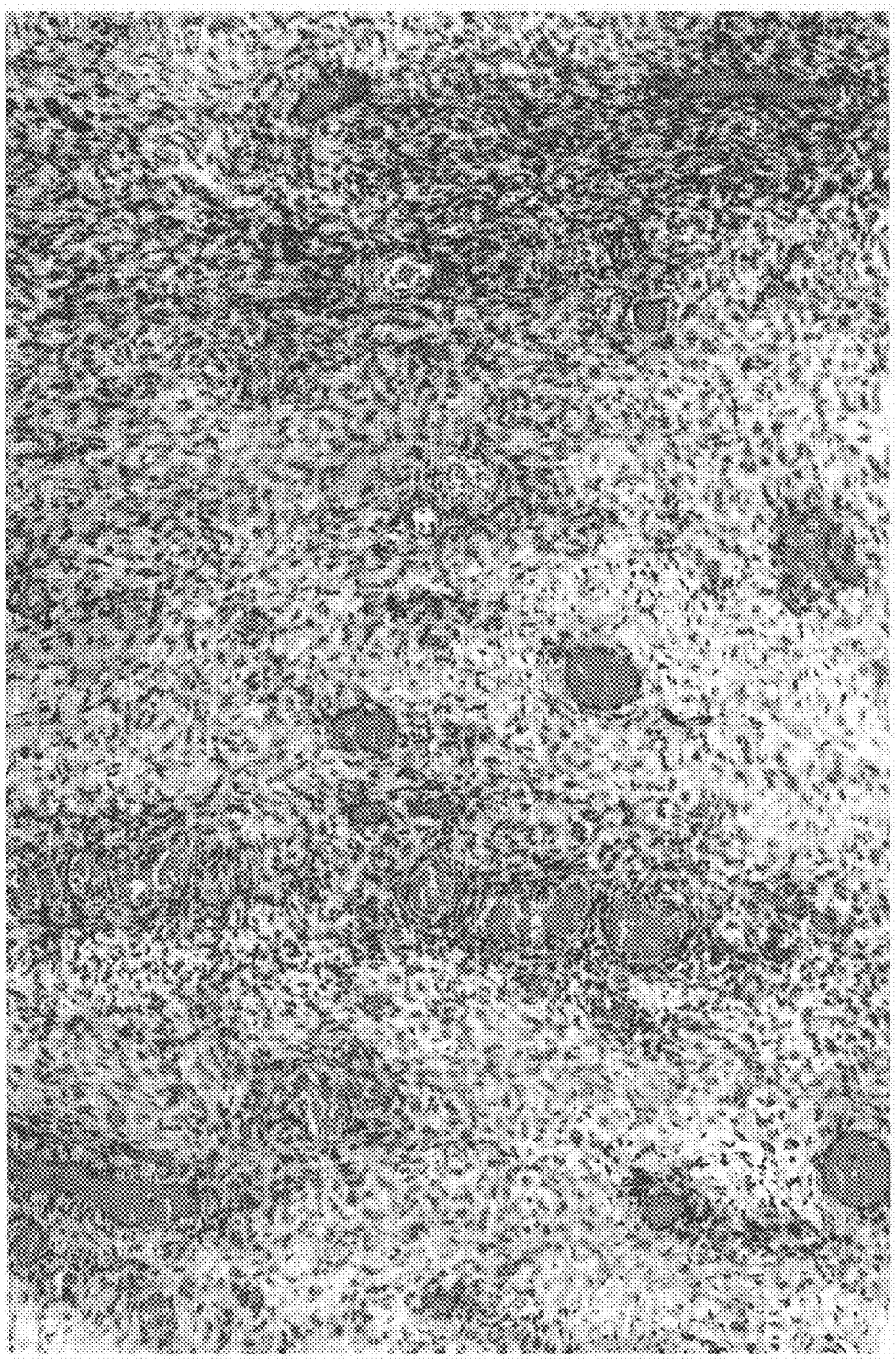
Fig. 11: With Product, Myometrium – MP (100X)

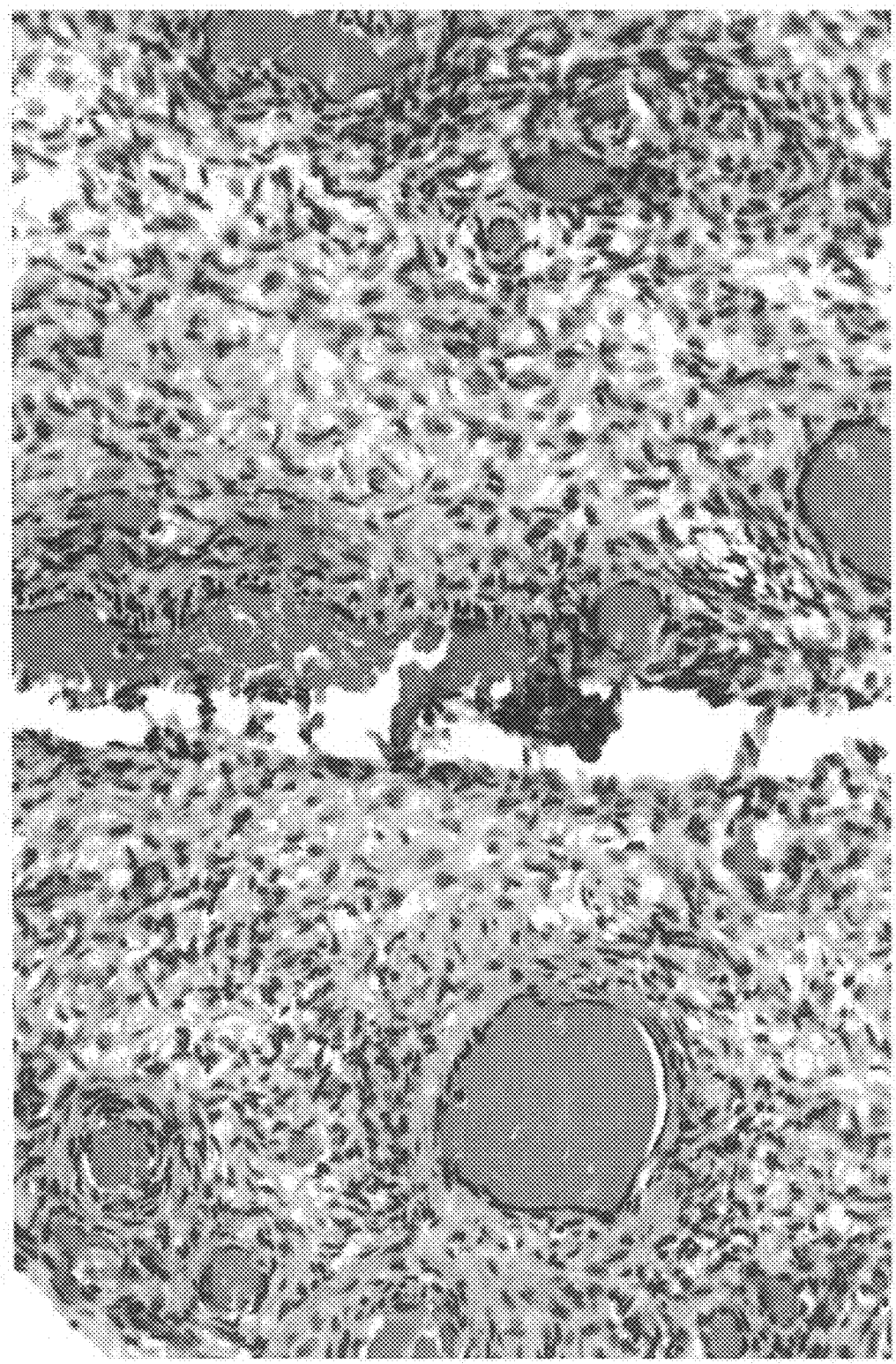
Fig. 12: Without Product, Myometrium – HP (400X)

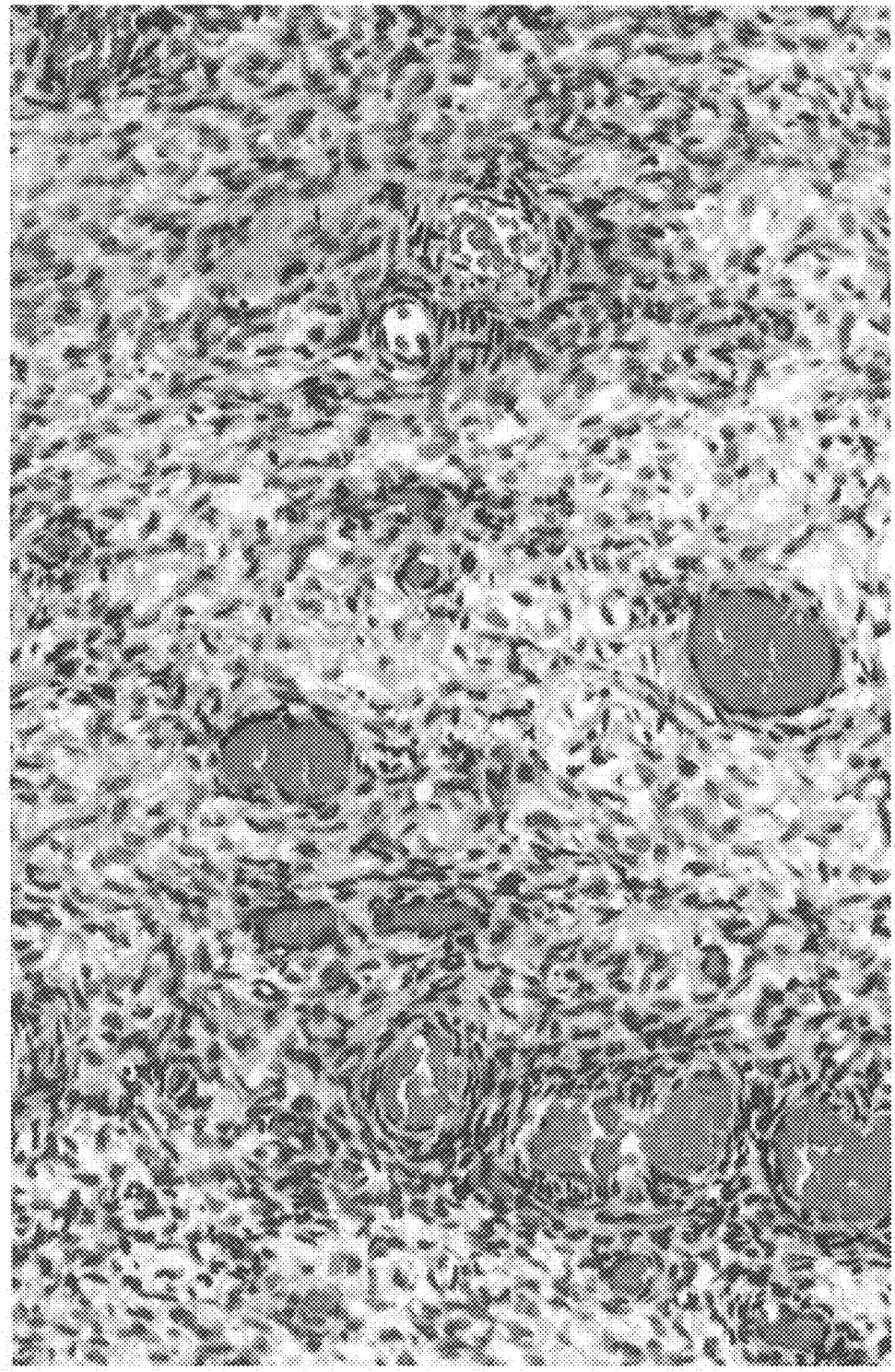
Fig. 13: With Product, Myometrium – HP (400X)

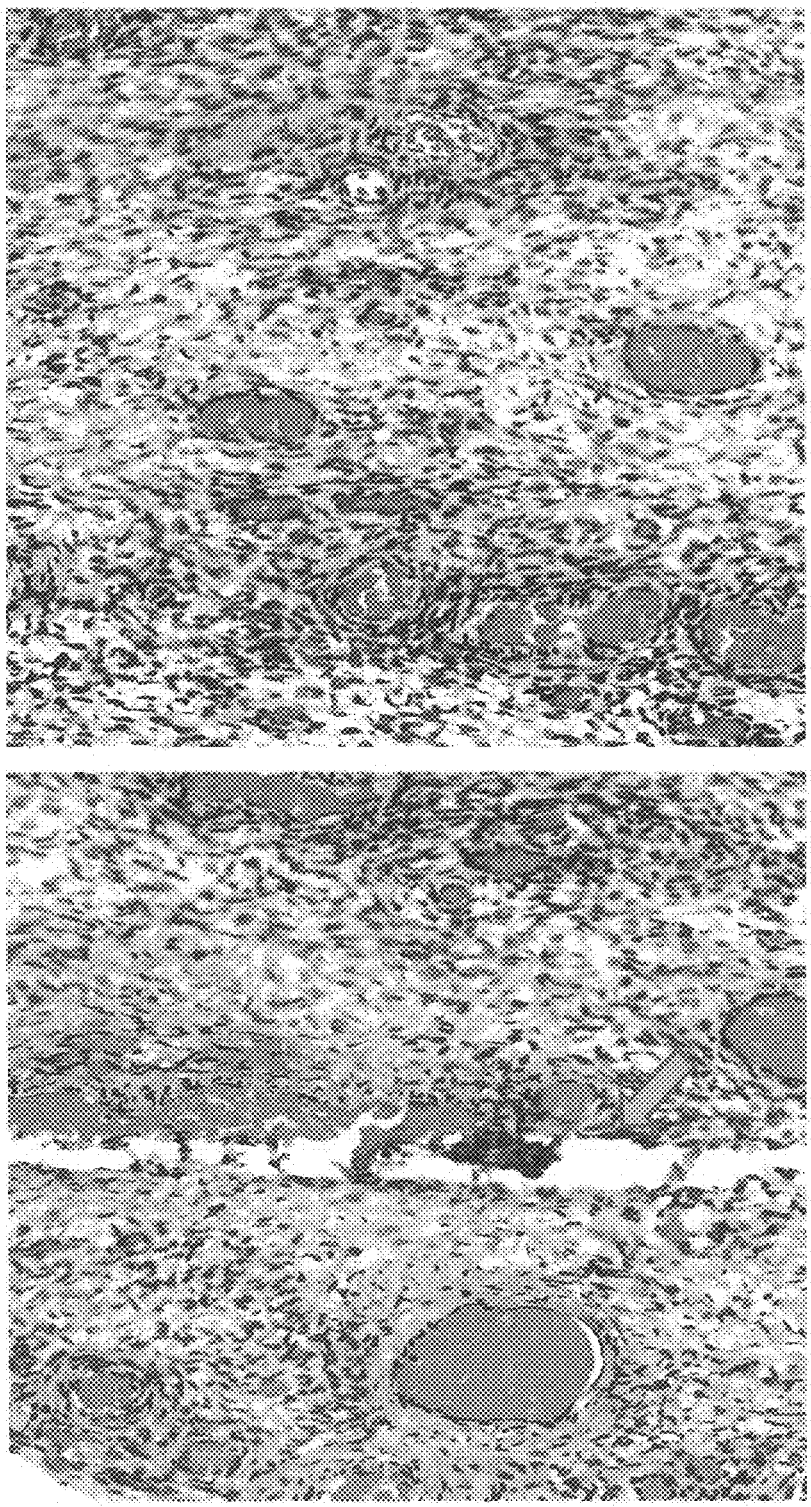

Fig. 15: Without Product, Prostate— LP (40X)

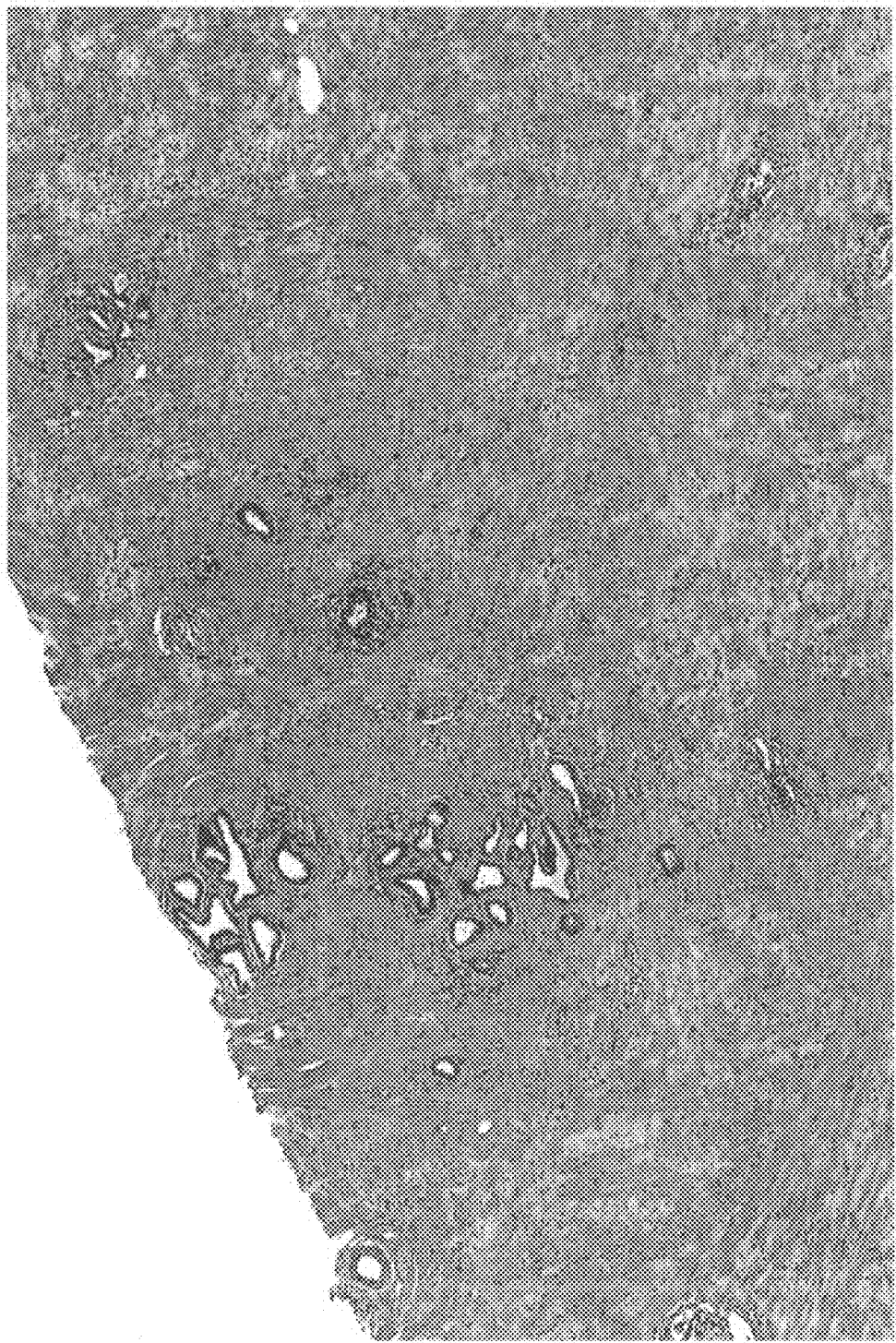
Fig. 16: With Product, Prostate– LP (40X)

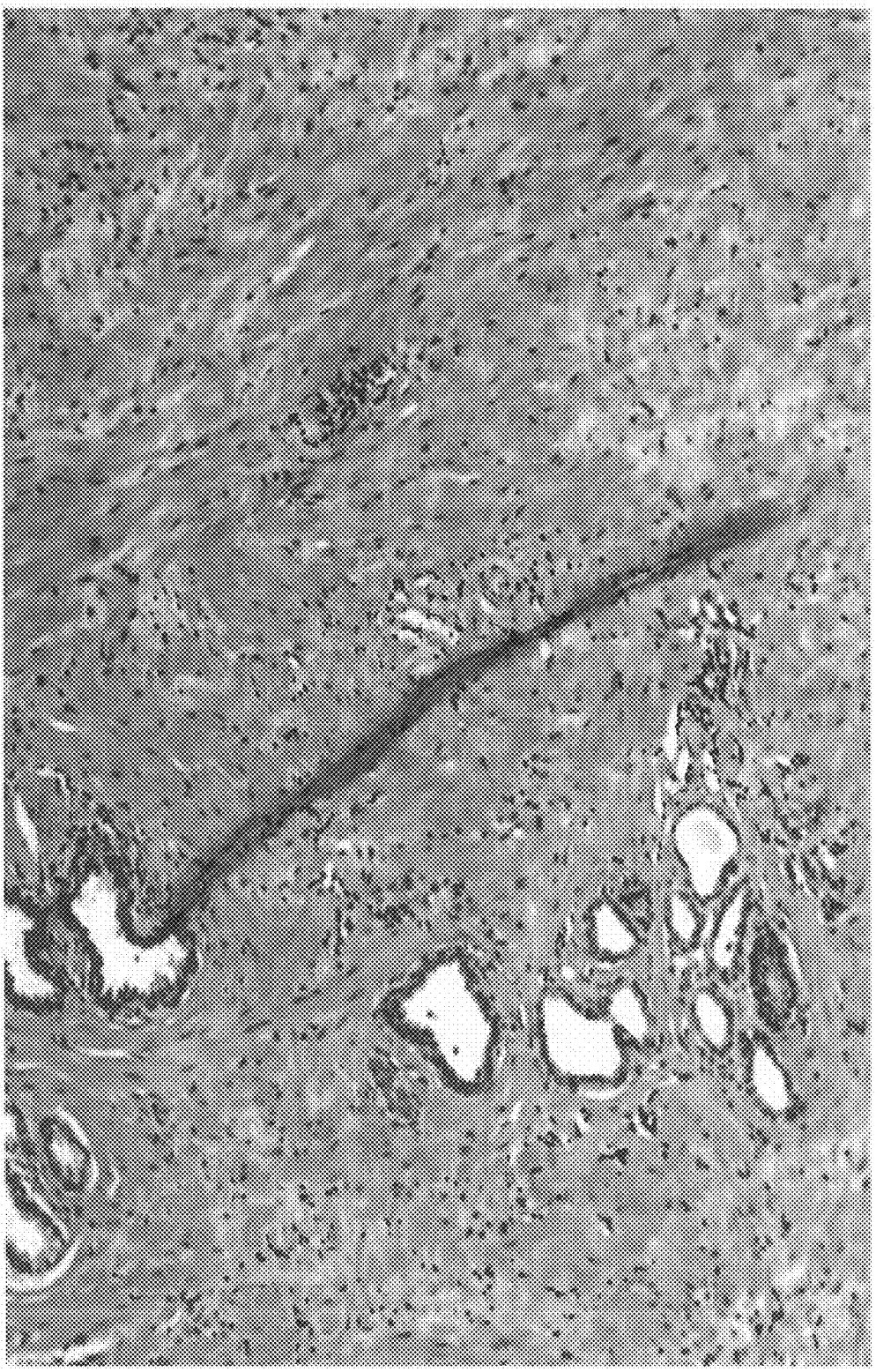
Fig. 17: Without Product, Prostate— MP (100X)

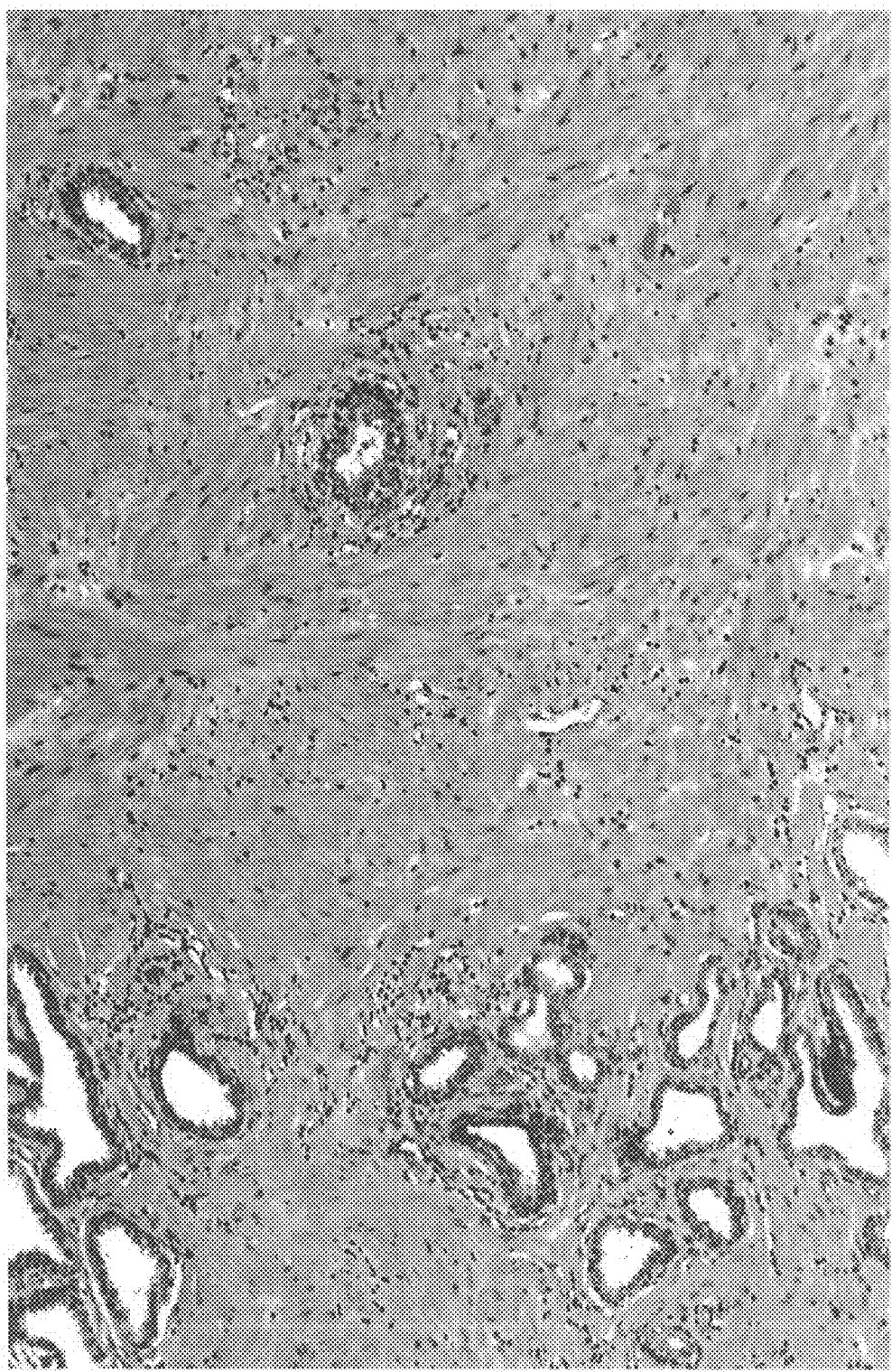
Fig. 18: With Product, Prostate– MP (100X)

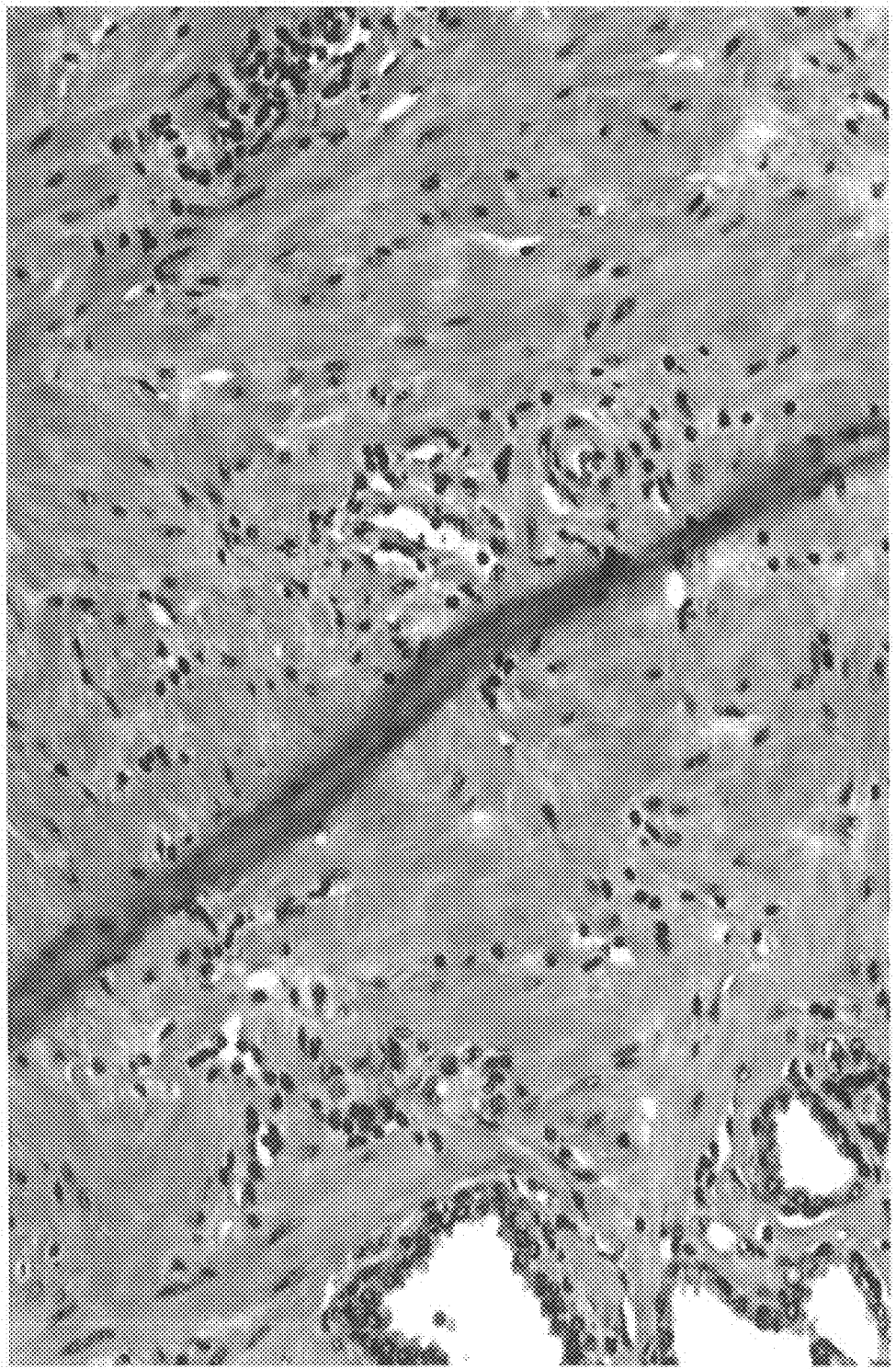

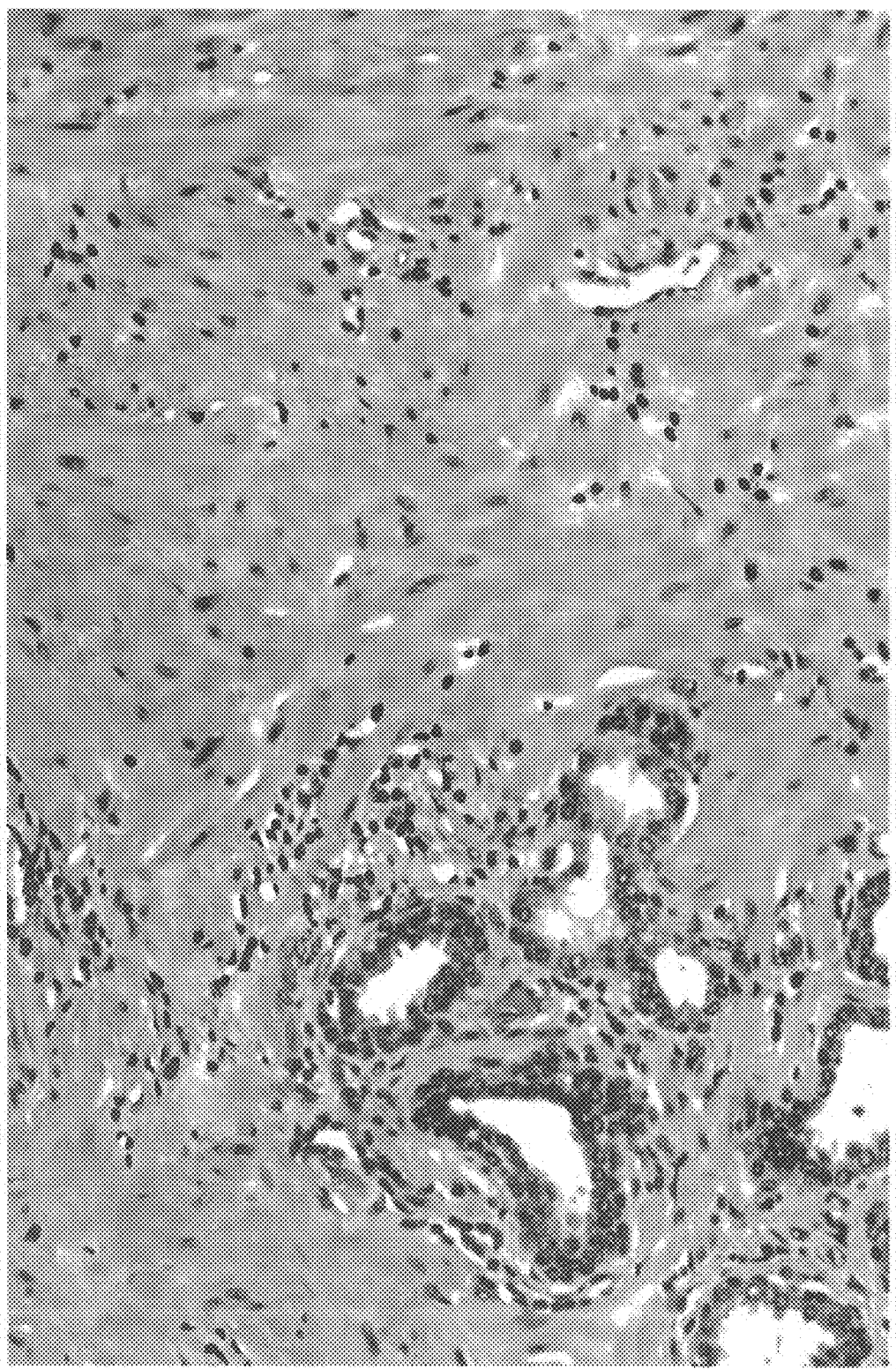
Fig. 20: With Product, Prostate— HP (400X)

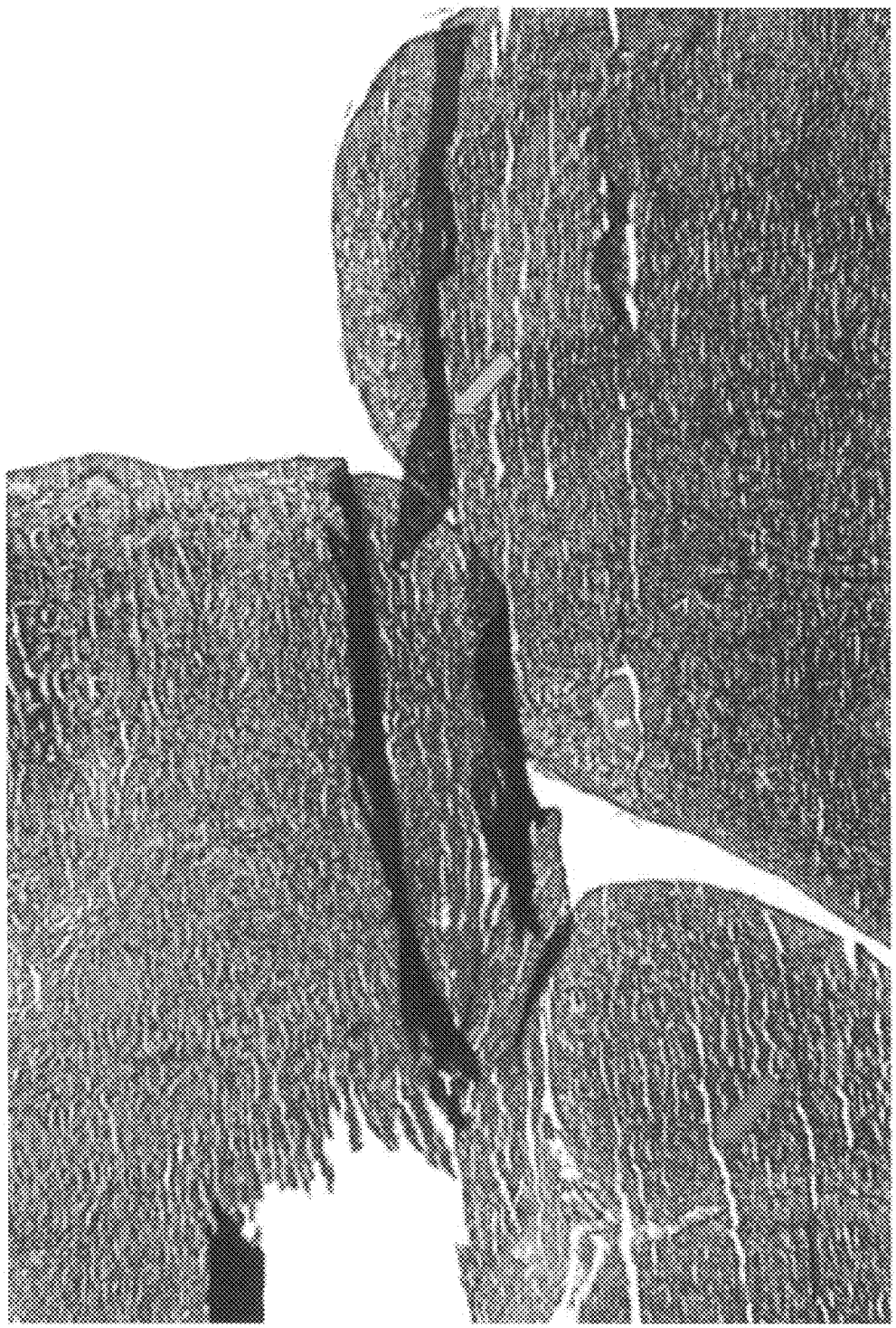
Fig. 21: Without Product, Tonsil – LP (40X)

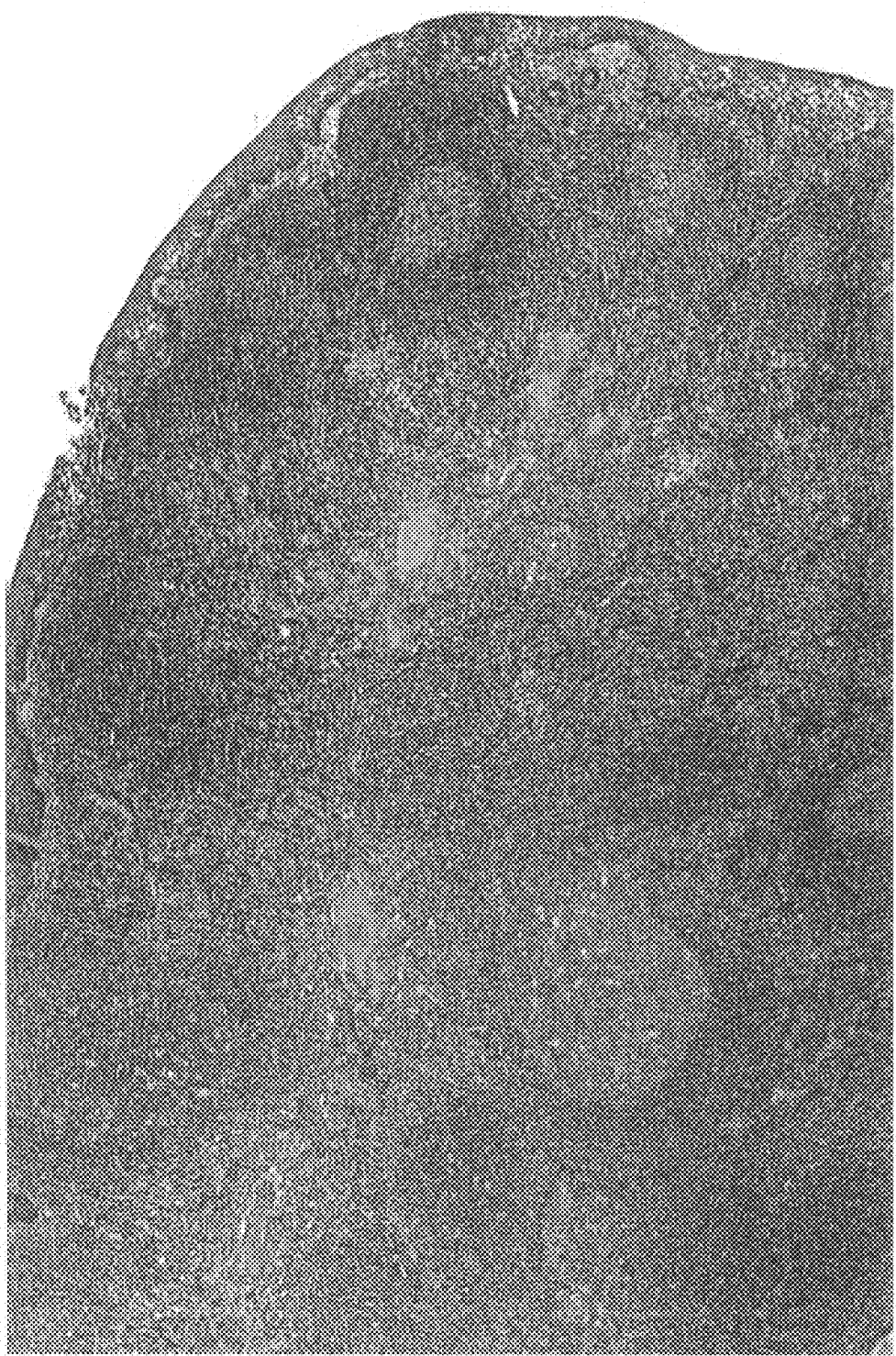
Fig. 22: With Product, Tonsil – LP (40X)

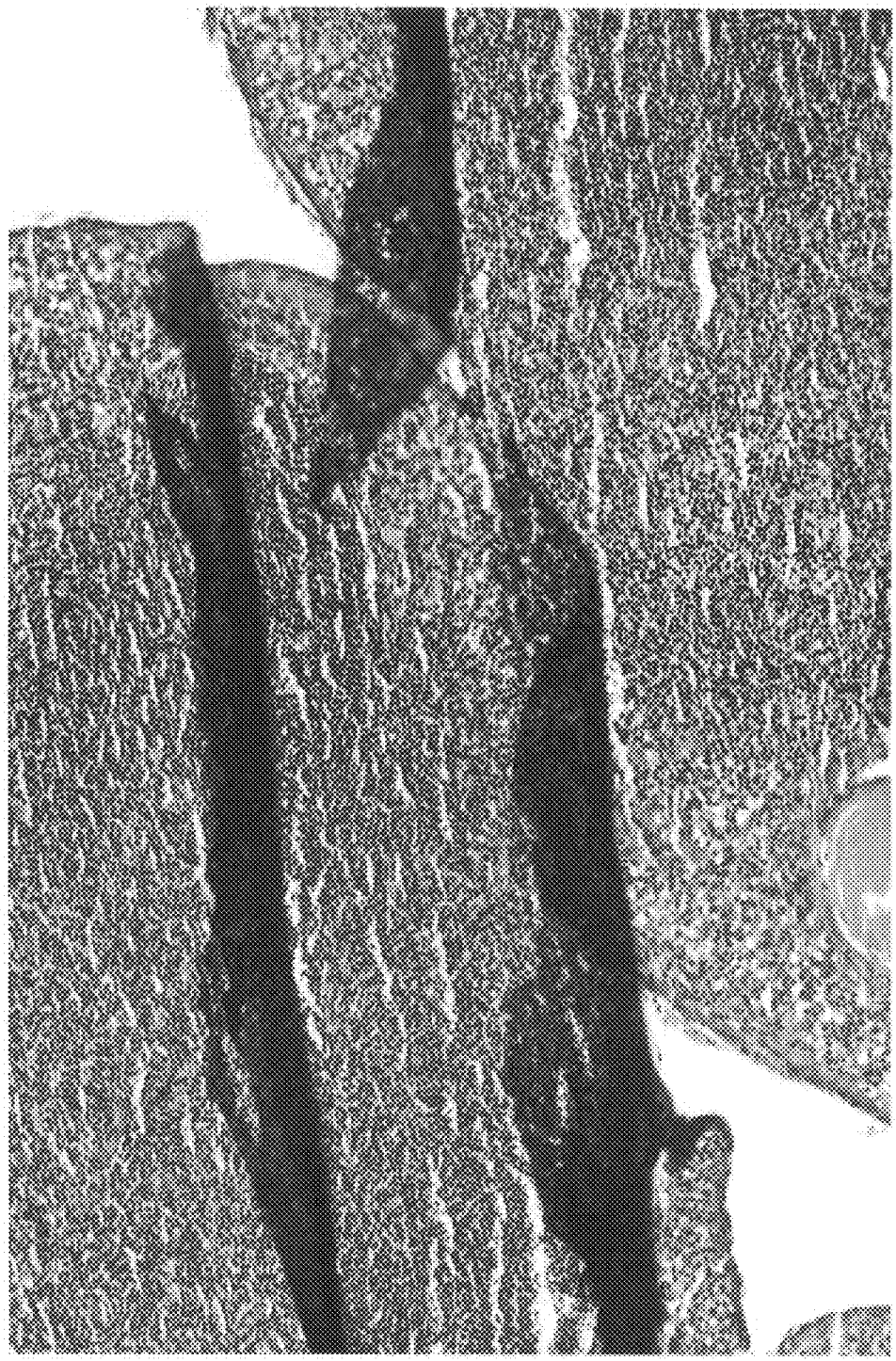
Fig. 23: Without Product, Tonsil – MP (100X)

Fig. 24: With Product, Tonsil – MP (100X)

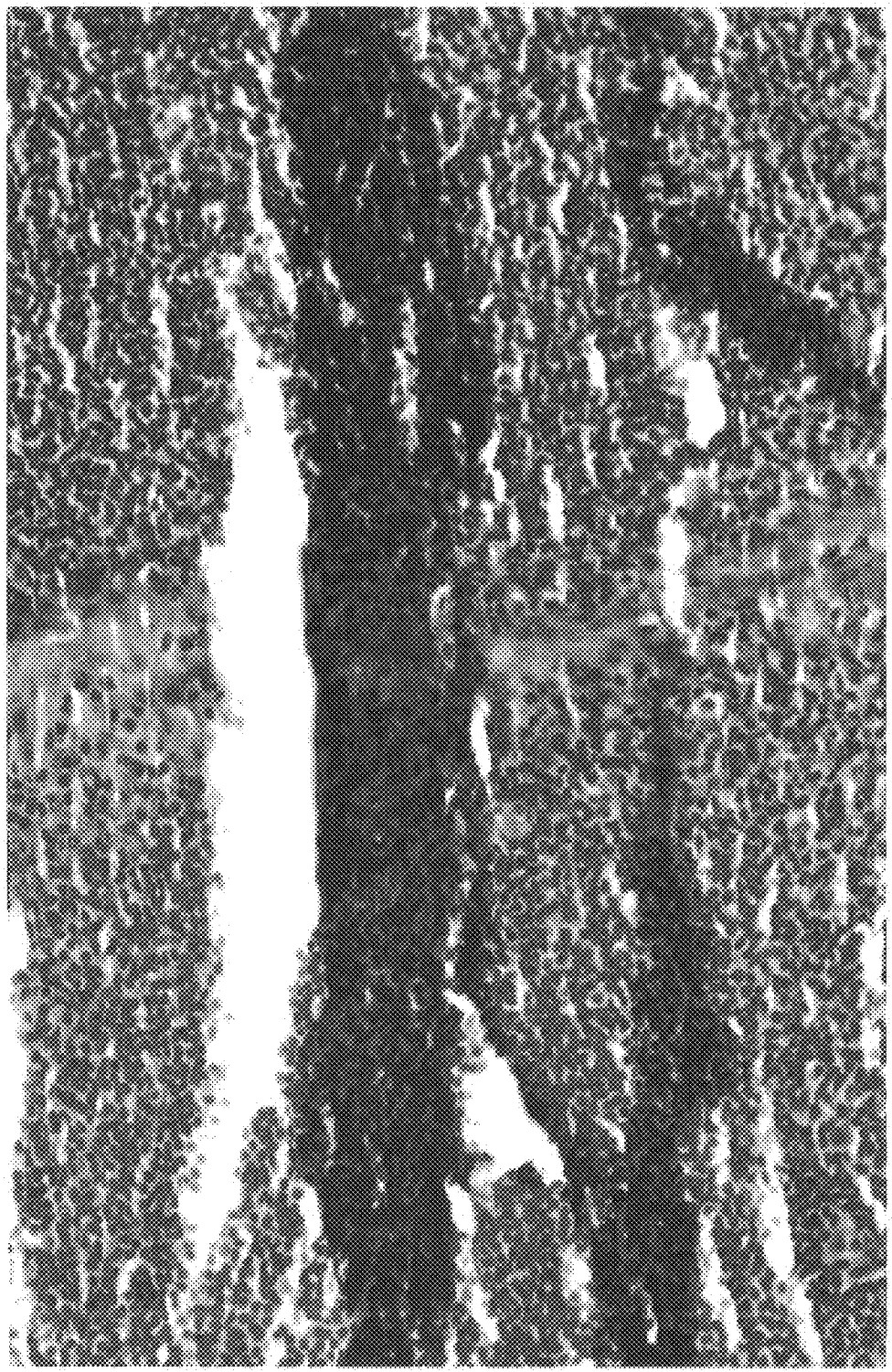
Fig. 25: Without Product, Tonsil – HP (400X)

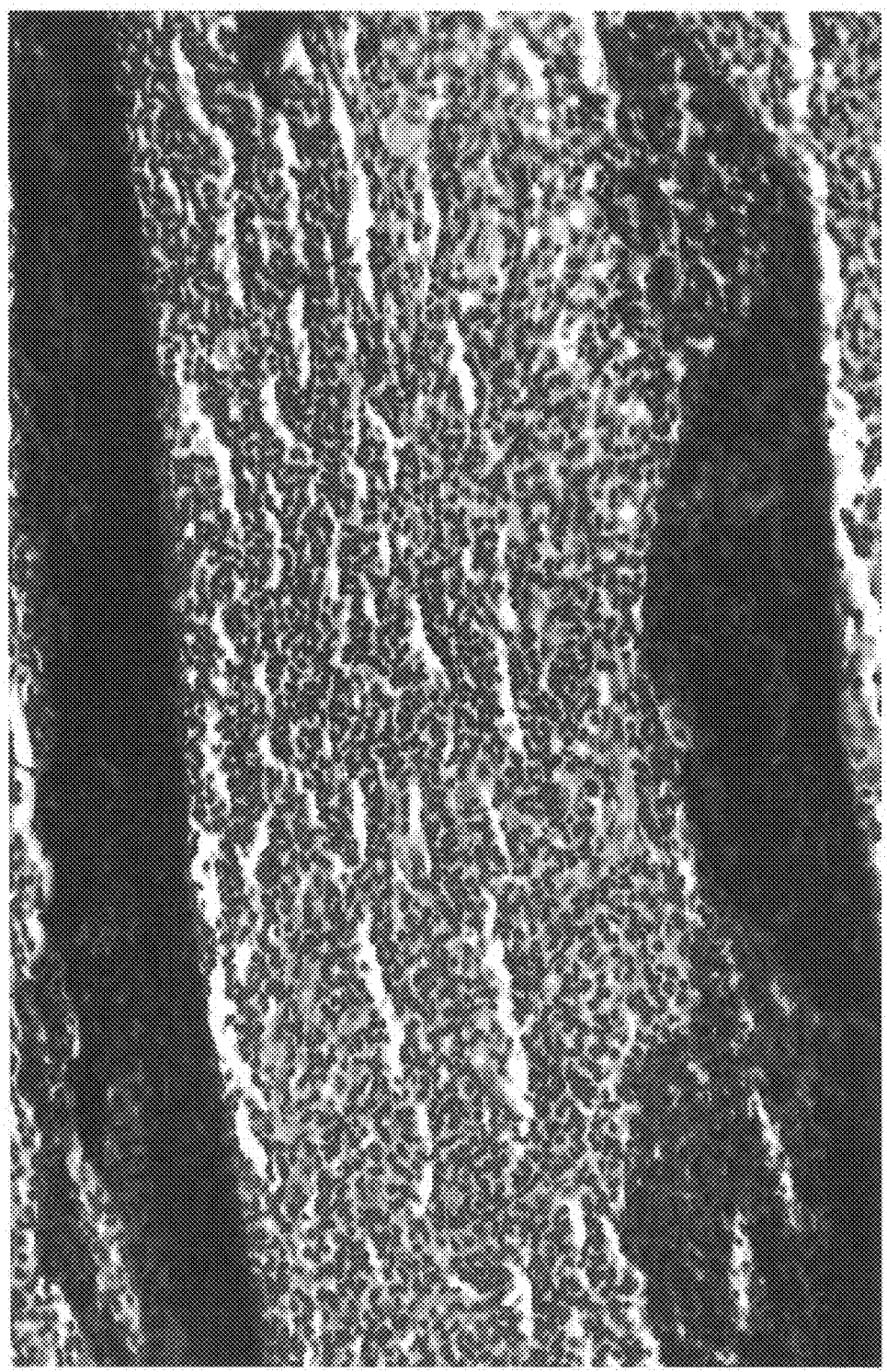
Fig. 26: Without Product, Tonsil – HP (400X)

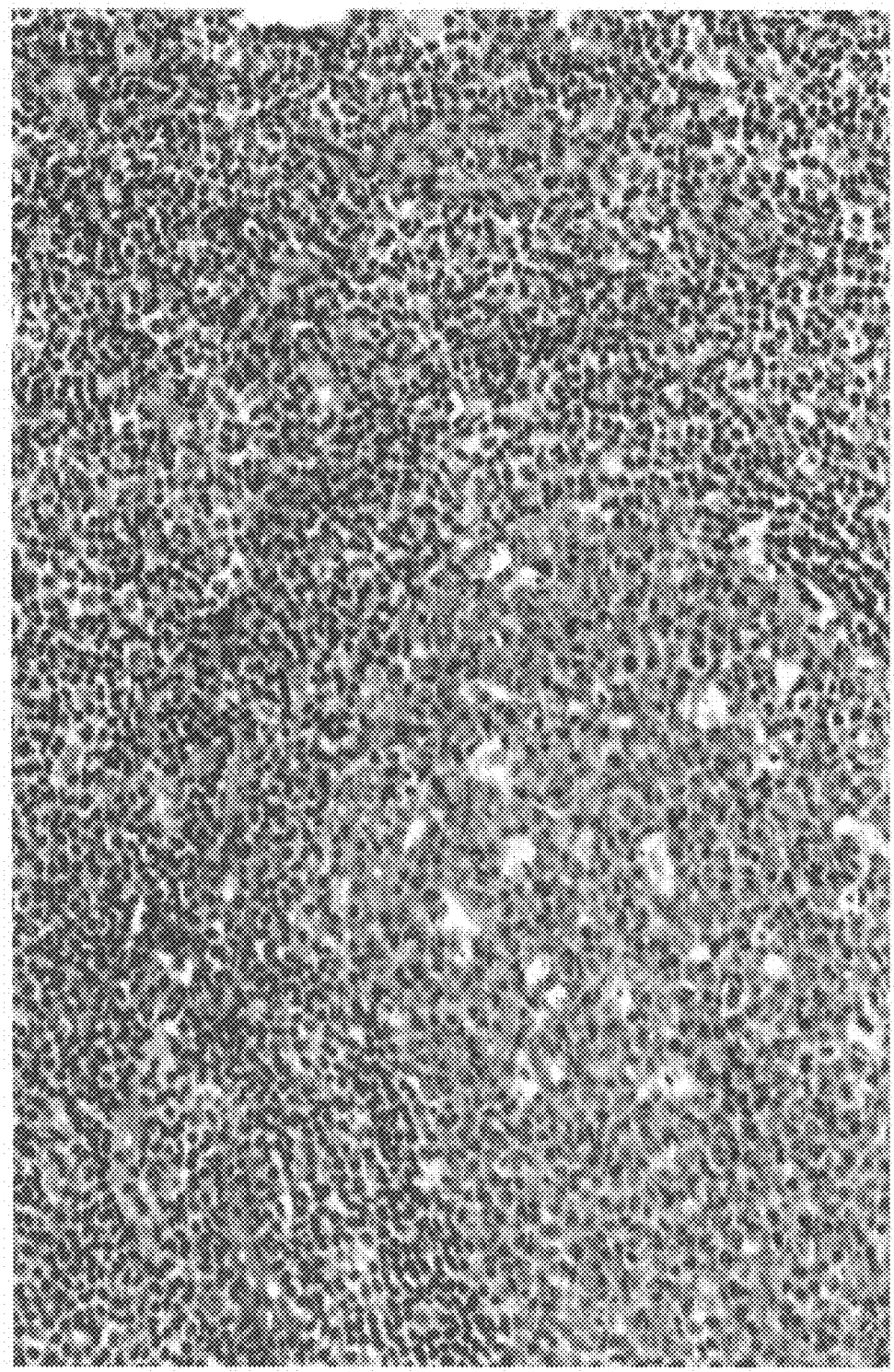
Fig. 27: With Product, Tonsil – HP (400X)

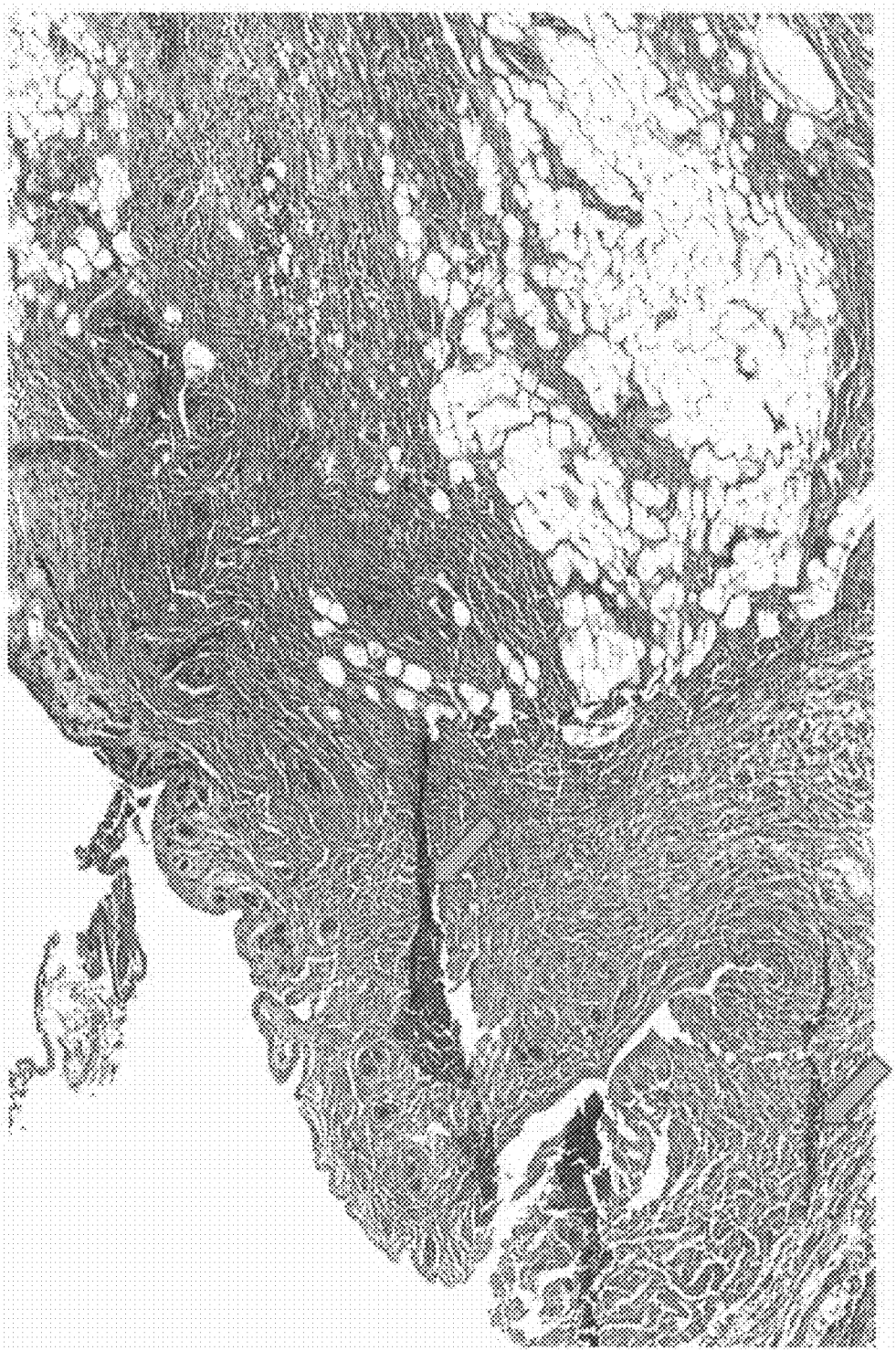
Fig. 28: Without Product, Hernia Sac – LP (40X)

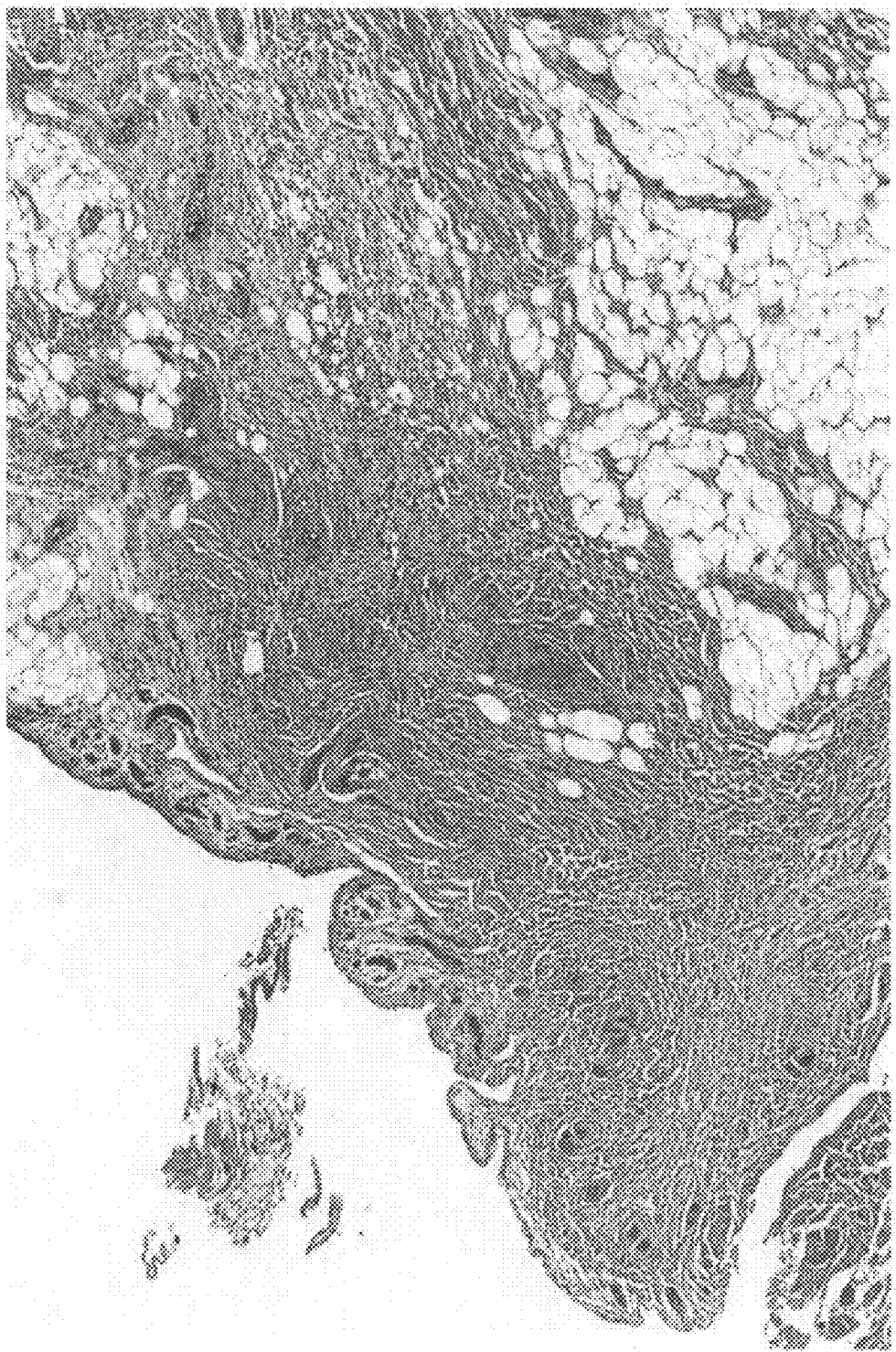
Fig. 29: With Product, Hernia Sac – LP (40X)

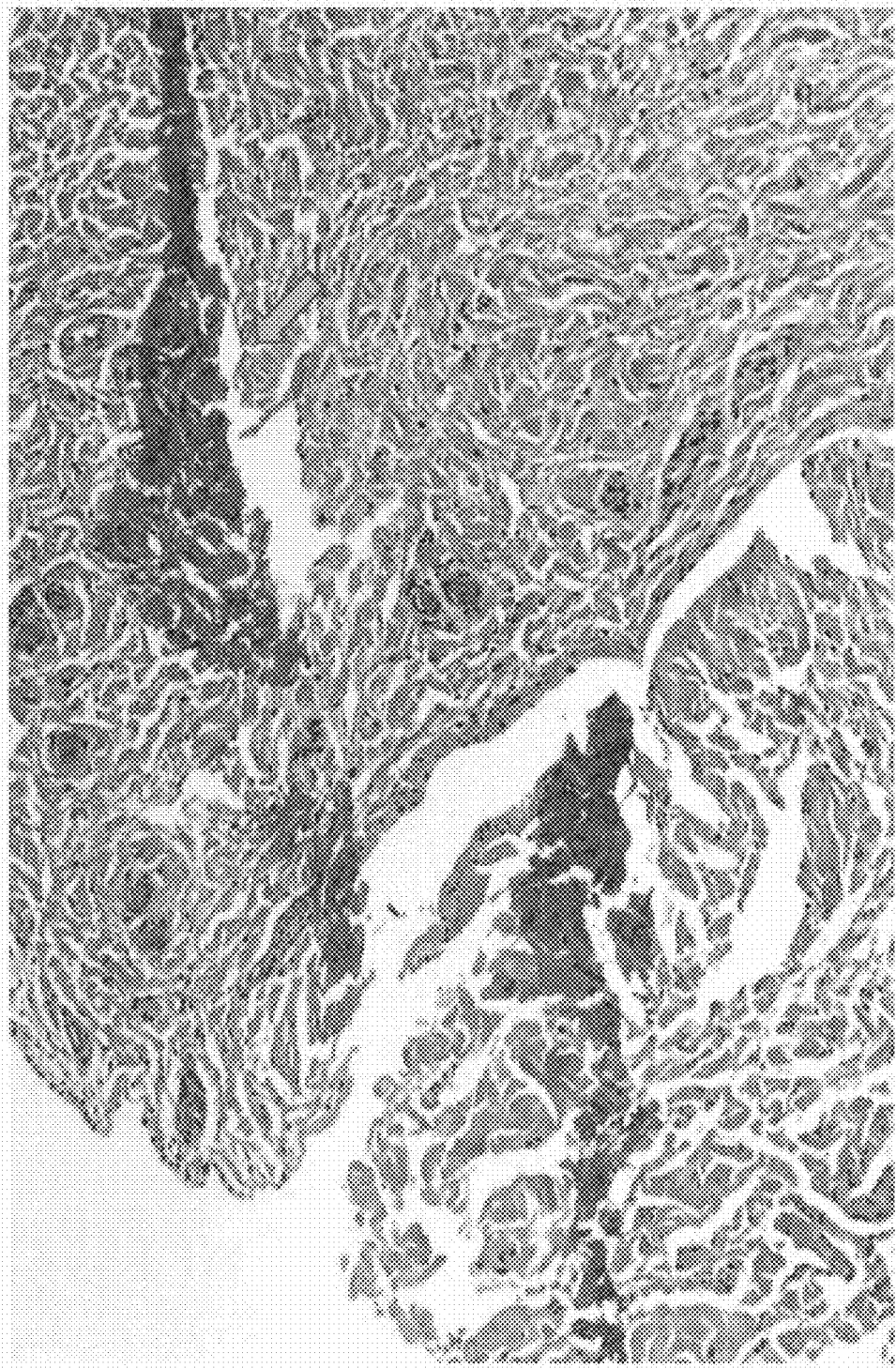
Fig. 30: Without Product, Hernia Sac – MP (100X)

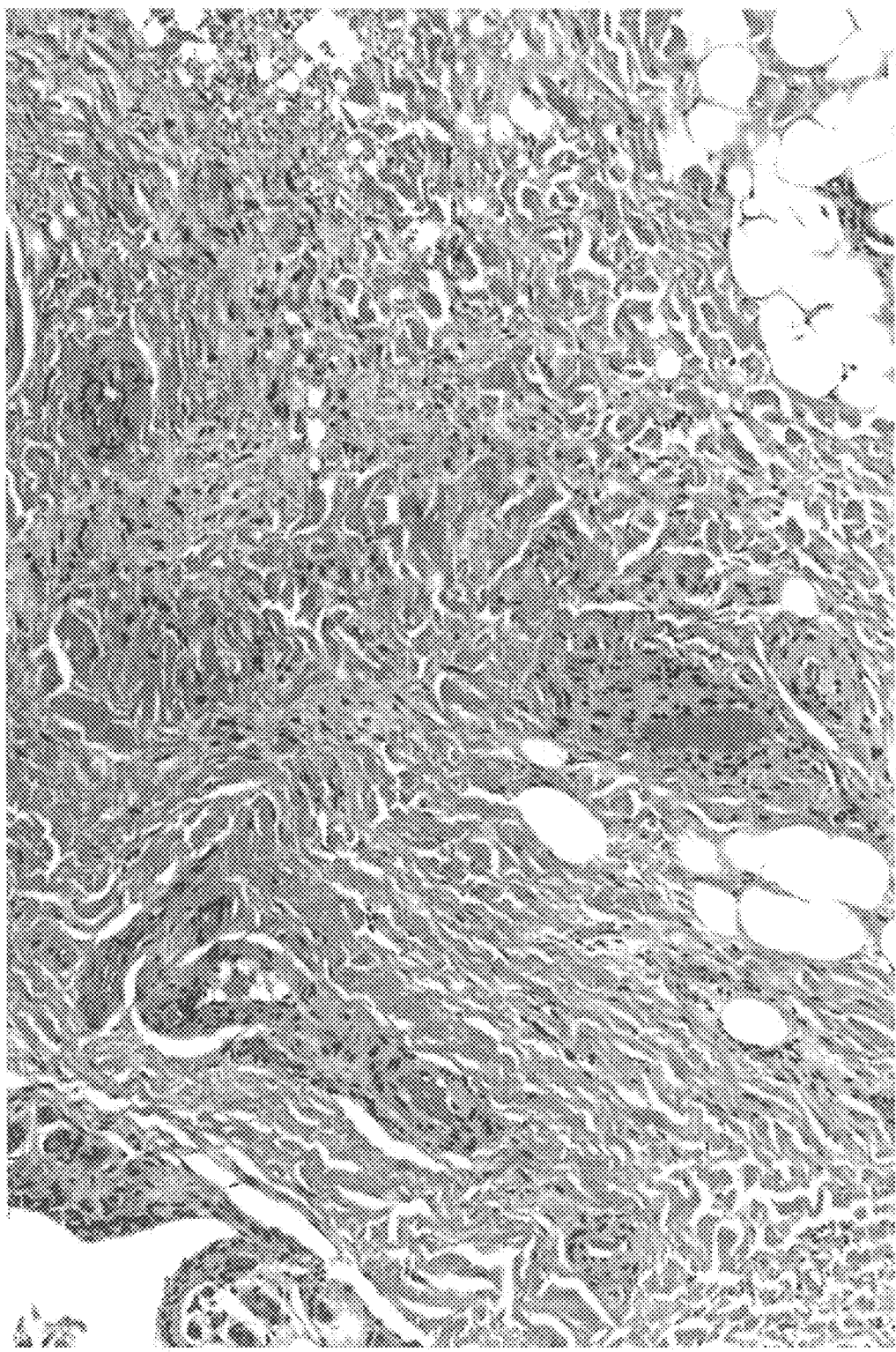
Fig. 31: With Product, Hernia Sac – MP (100X)

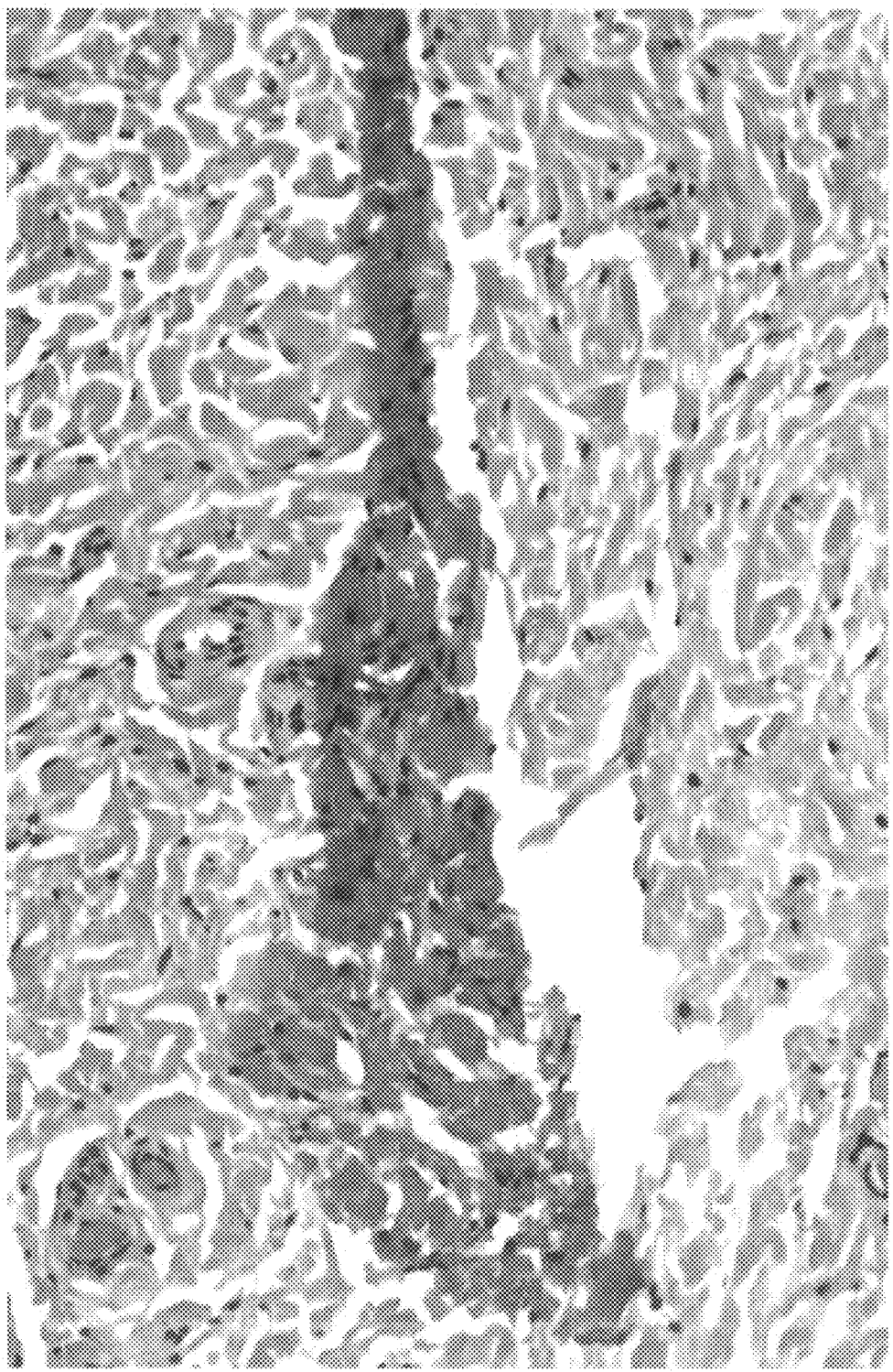
Fig. 32: Without Product, Hernia Sac – HP (400X)

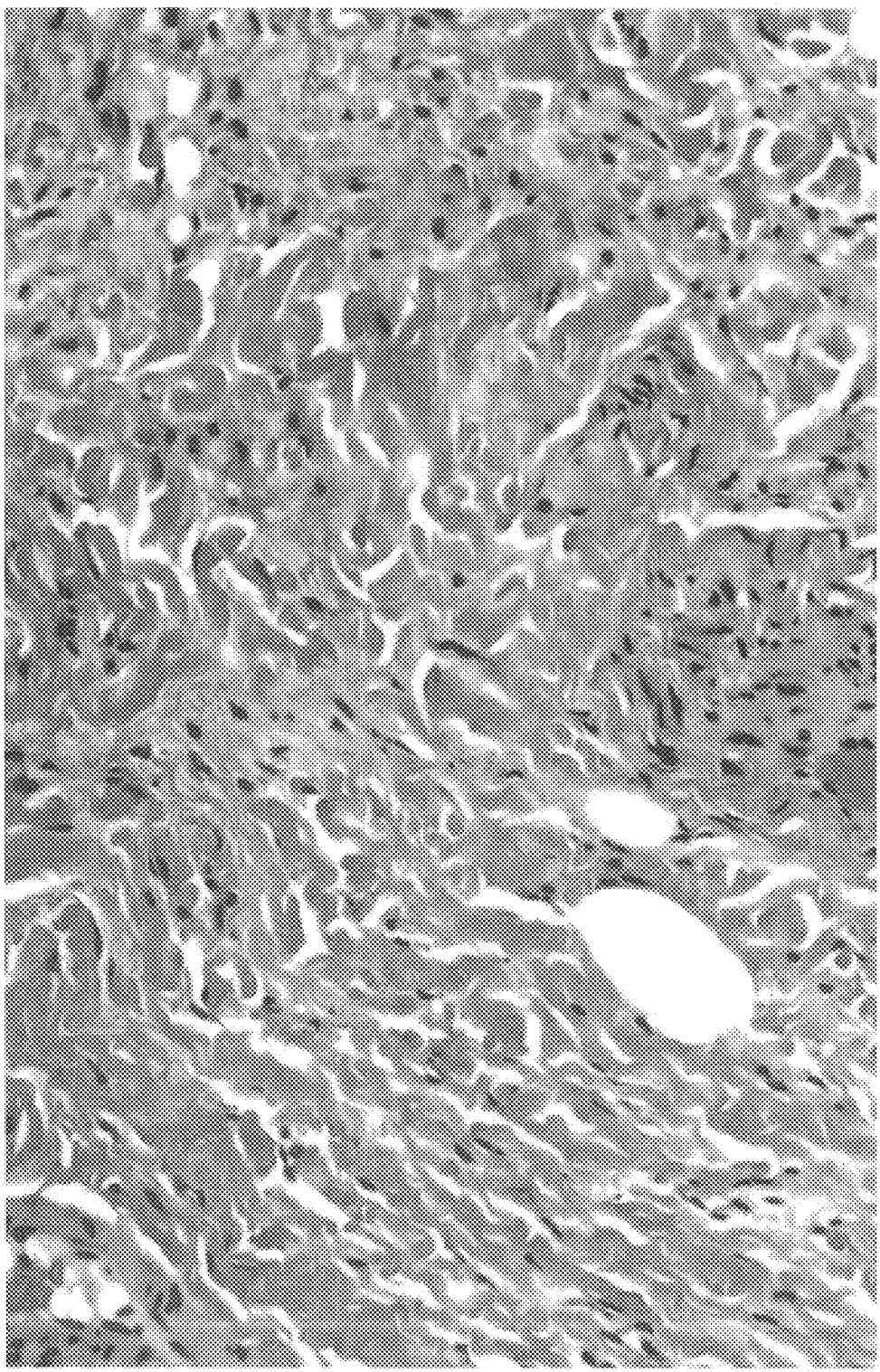
Fig. 33: With Product, Hernia Sac – HP (400X)

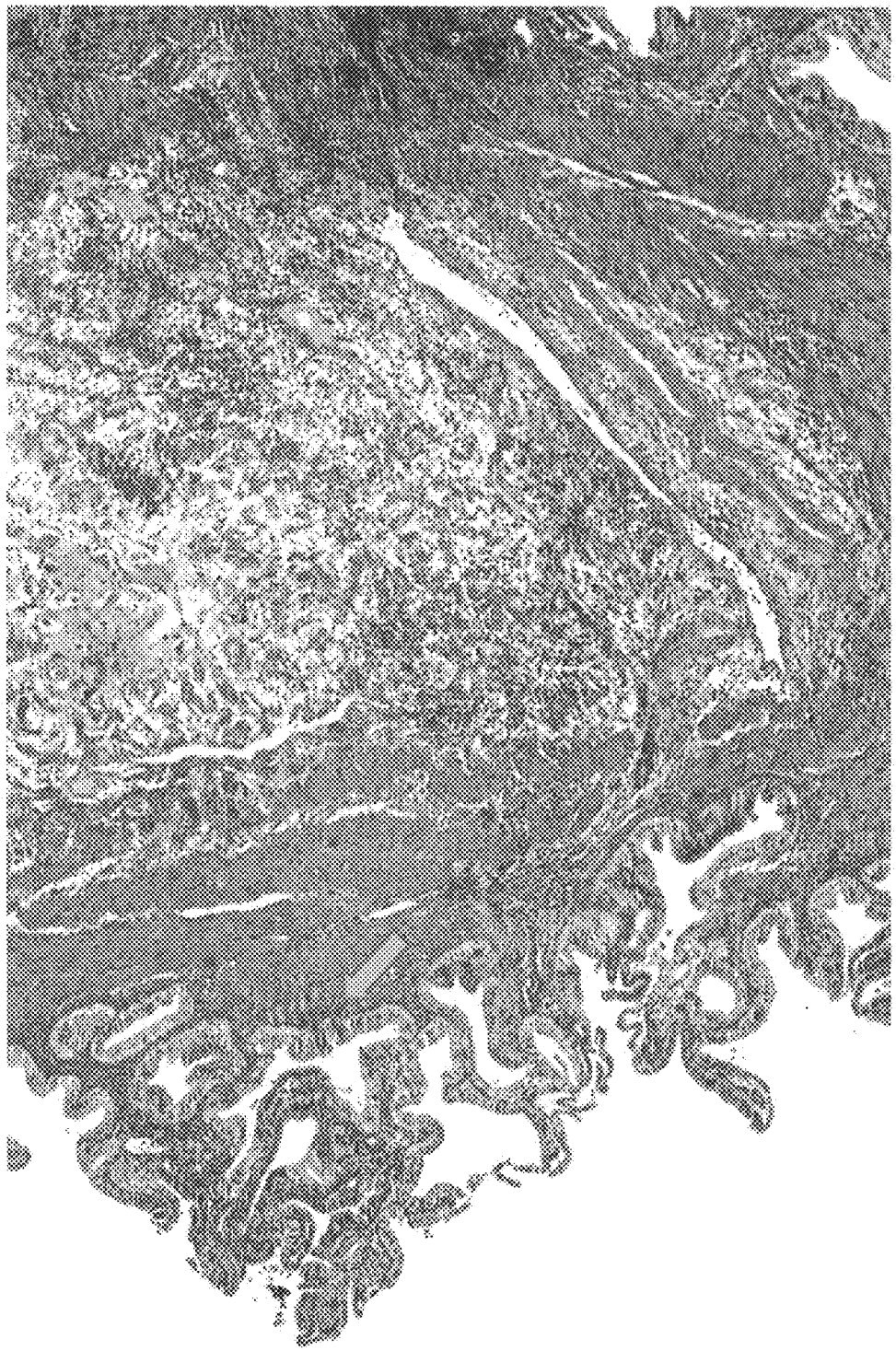
Fig. 34: Without Product, Gallbladder – LP (40X)

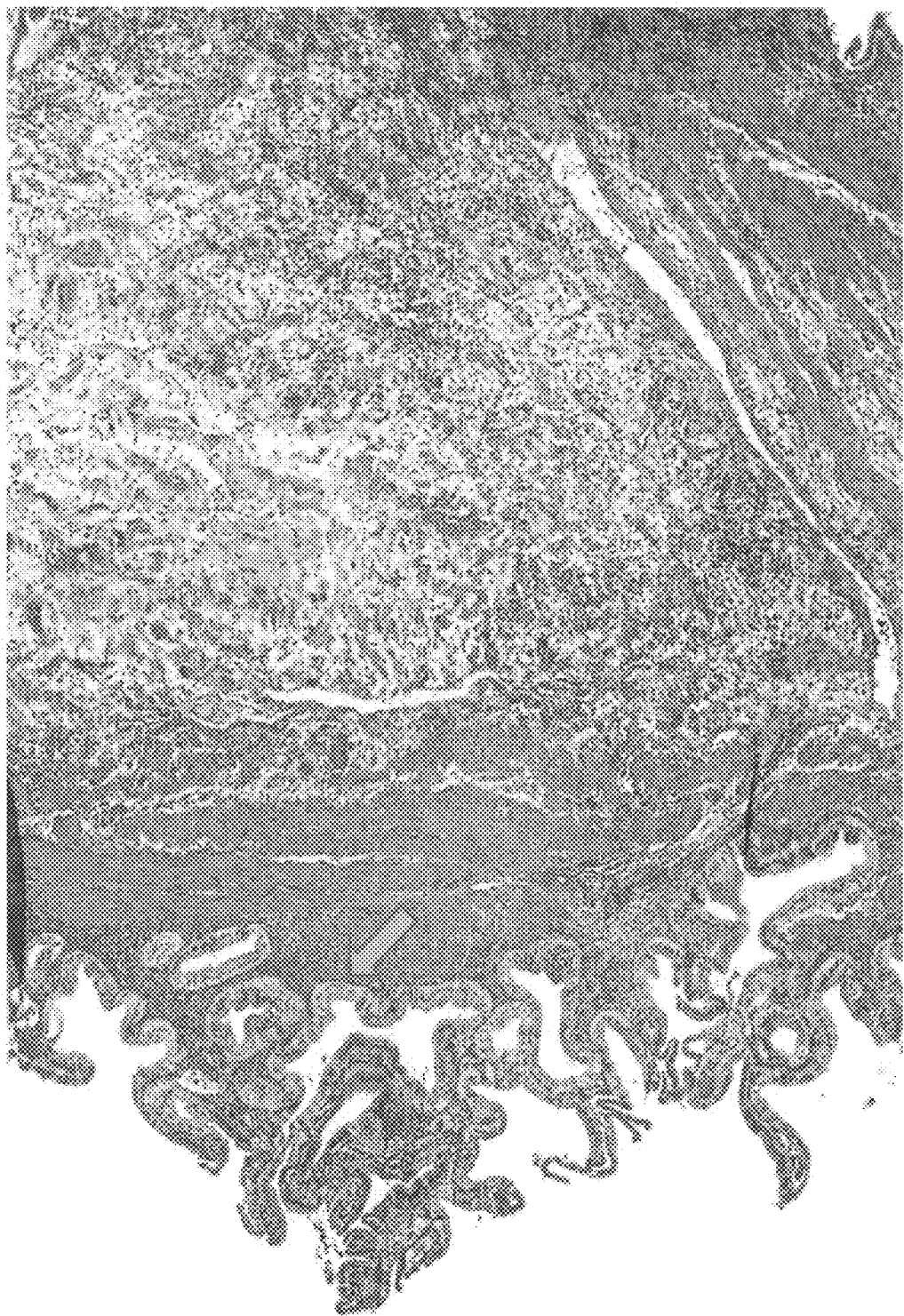
Fig. 35: With Product, Gallbladder – LP (40X)

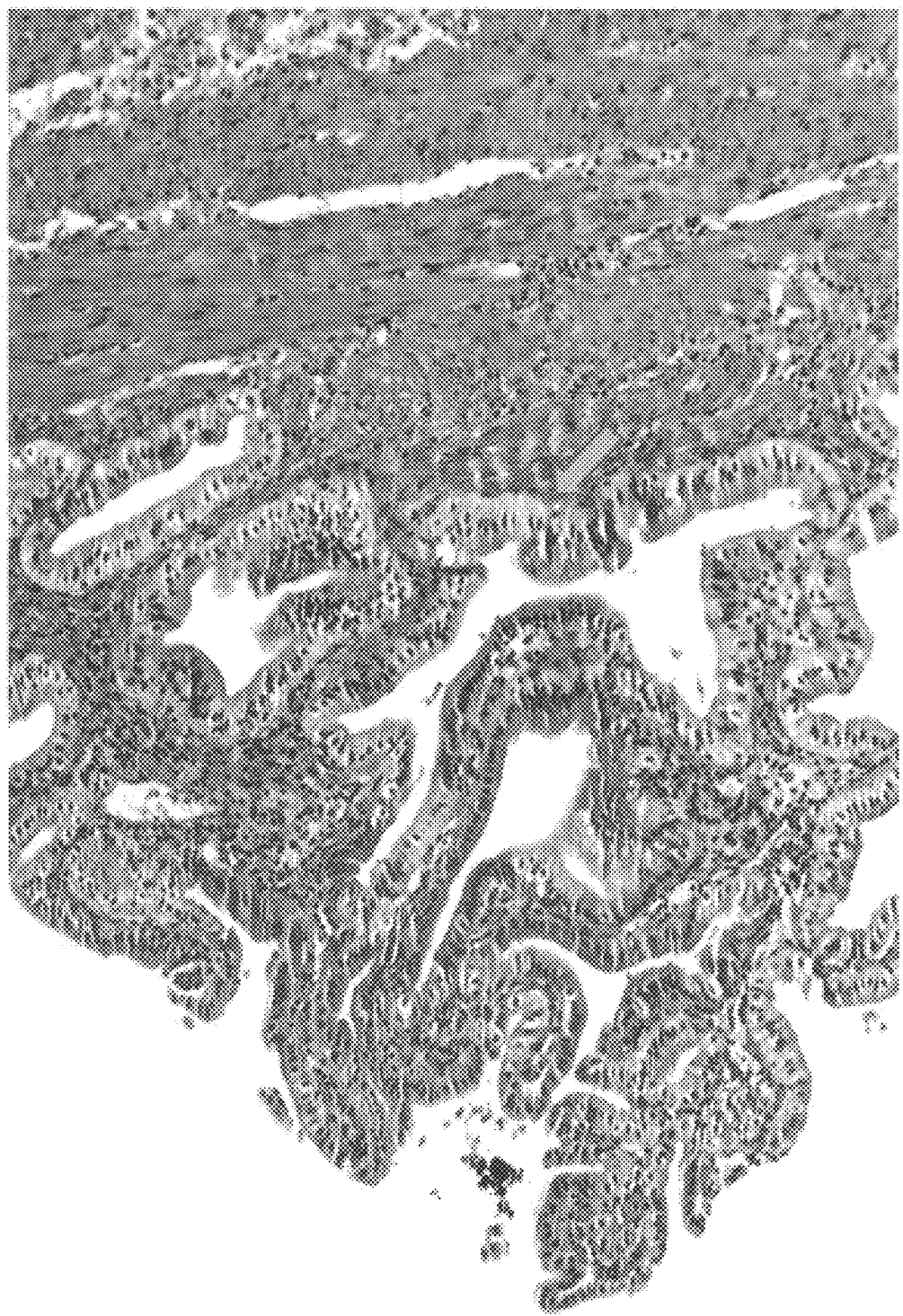
Fig. 36 Without Product, Gallbladder – MP (100X)

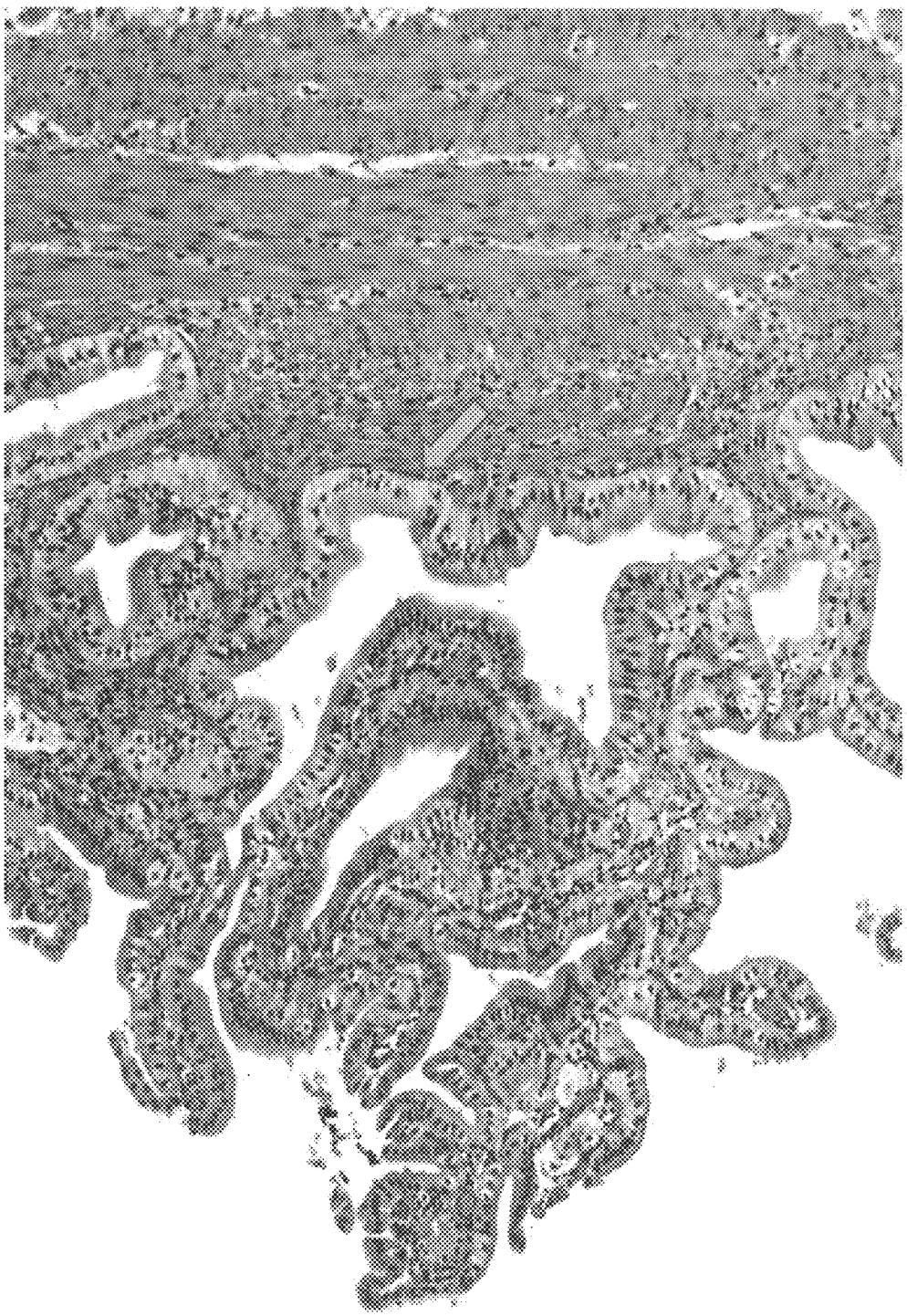
Fig. 37: With Product, Gallbladder – MP (100X)

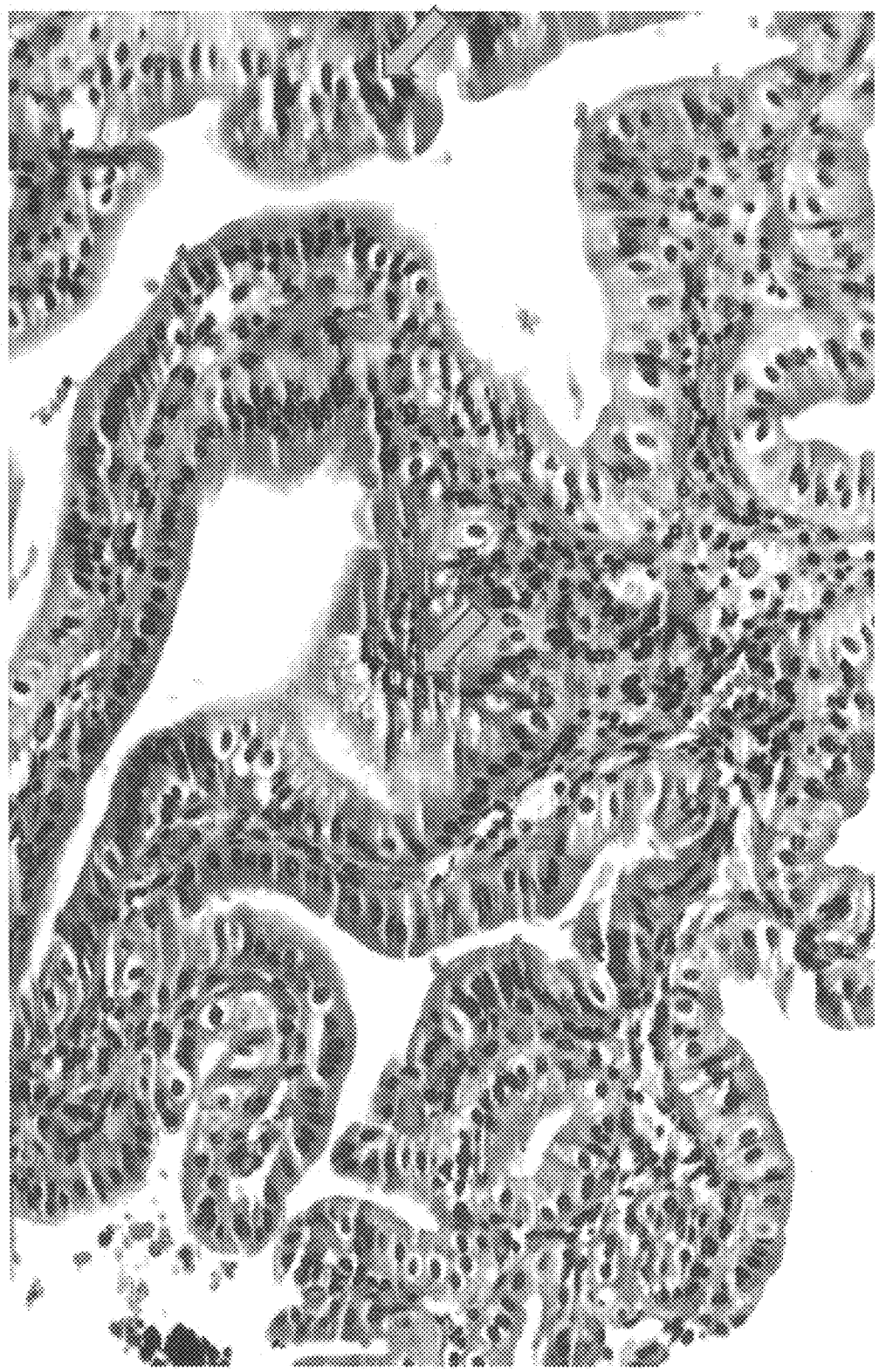
Fig. 38: Without Product, Gallbladder – HP (400X)

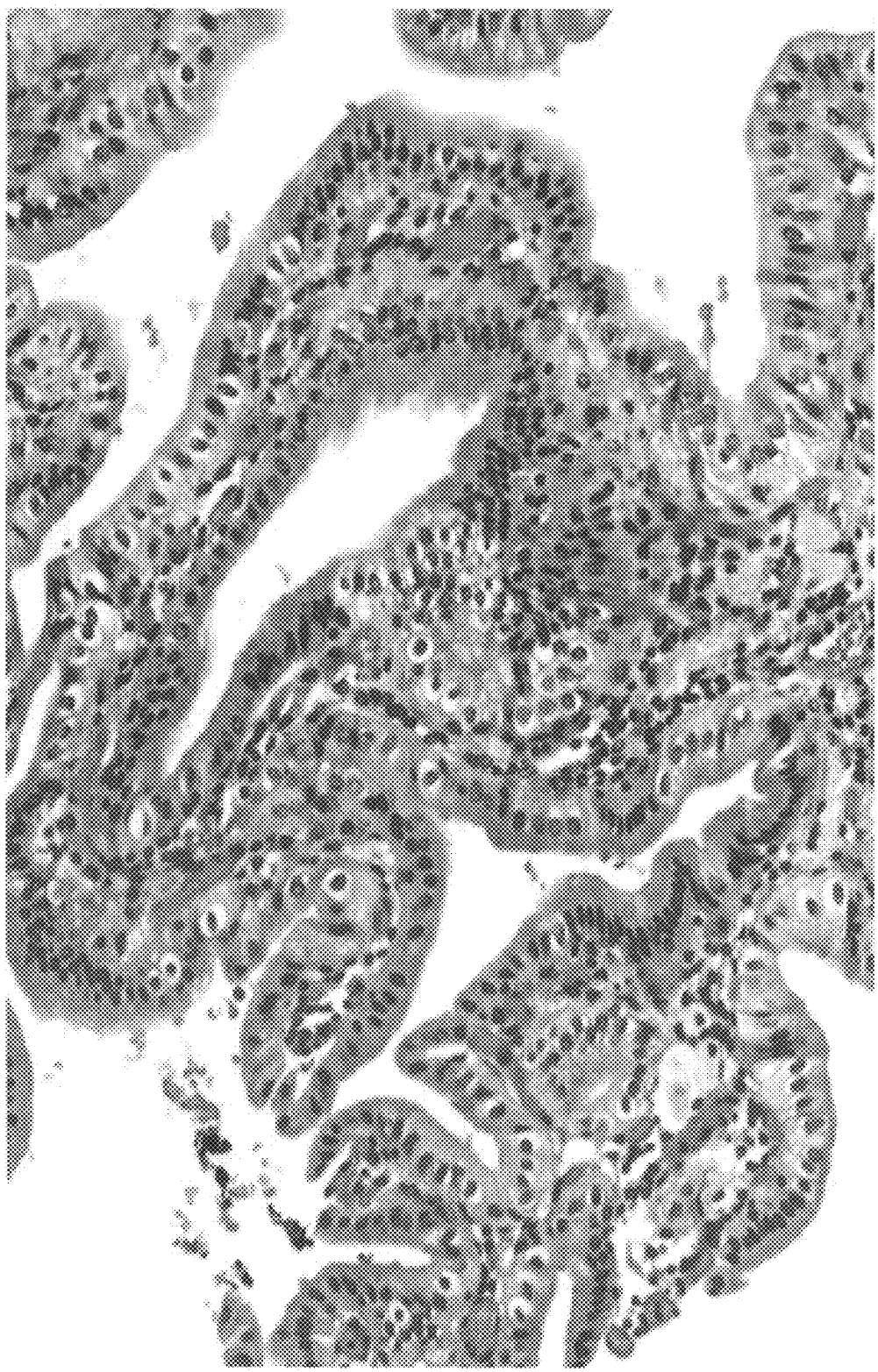
Fig. 39: With Product, Gallbladder – HP (400X)

AQUEOUS COMPOSITIONS AND METHODS OF USING THE SAME FOR HISTOPATHOLOGICAL EVALUATION OF TISSUE SAMPLES

BACKGROUND OF THE INVENTION

Tissue samples are routinely prepared during pathological studies. One aspect of tissue preparation is the use of tissue softeners to prepare tissue samples for pathologic evaluation. The softeners rehydrate the tissue at least to the point where the tissue can be mechanically processed using standard histotechnologic methods. One example of this mechanical preparation is in the cutting of the tissue sample to a size appropriate for use, and the use of the softener allows for cutting of the tissue without further damage to the tissue.

Known softeners are available that sufficiently soften the tissue for processing and evaluation. These known softeners, however, include flammable solvents such as methanol and ethanol, and the flammable nature of these softeners poses an environmental hazard to researchers that perform the histopathologic studies and the laboratories where these studies are performed.

In view of the foregoing, there is a need for tissue softeners useful in the field of histopathologic studies that do not contain flammable solvent yet are able to meet the requirements of tissue softeners in this field.

BRIEF DESCRIPTION OF THE INVENTION

One object of the invention is to provide a softener useful for preparing tissue samples for pathological studies that sufficiently rehydrates and/or softens the tissue, where the softener does not contain flammable solvents.

This and other objects are achieved with an aqueous solution that comprises:
 (A) an organic polyol having from 2 to 20 carbon atoms and having a flash point of at least 93° C.;
 (B) a base;
 (C) a surfactant; and
 (D) water,
wherein the aqueous solution does not include an organic solvent having a flash point below 23° C. and a boiling point of at least 38° C.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 represents a picture of a sample of endometrium tissue that was prepared without the use of an aqueous composition according to the present invention, the picture taken at 40× magnification.

FIG. 2 represents a picture of a sample of endometrium tissue that was prepared with the use of an aqueous composition according to the present invention, the picture taken at 40× magnification.

FIG. 3 represents a comparison of the tissue samples of FIGS. 1 and 2.

FIG. 4 represents a picture of a sample of endometrium tissue that was prepared without the use of an aqueous composition according to the present invention, the picture taken at 100× magnification.

FIG. 5 represents a picture of a sample of endometrium tissue that was prepared with the use of an aqueous composition according to the present invention, the picture taken at 100× magnification.

FIG. 6 represents a picture of a sample of endometrium tissue that was prepared without the use of an aqueous composition according to the present invention, the picture taken at 400× magnification.

FIG. 7 represents a picture of a sample of endometrium tissue that was prepared with the use of an aqueous composition according to the present invention, the picture taken at 400× magnification.

FIG. 8 represents a picture of a sample of myometrium tissue that was prepared without the use of an aqueous composition according to the present invention, the picture taken at 40× magnification.

FIG. 9 represents a picture of a sample of myometrium tissue that was prepared with the use of an aqueous composition according to the present invention, the picture taken at 40× magnification.

FIG. 10 represents a picture of a sample of myometrium tissue that was prepared without the use of an aqueous composition according to the present invention, the picture taken at 100× magnification.

FIG. 11 represents a picture of a sample of myometrium tissue that was prepared with the use of an aqueous composition according to the present invention, the picture taken at 100× magnification.

FIG. 12 represents a picture of a sample of myometrium tissue that was prepared without the use of an aqueous composition according to the present invention, the picture taken at 400× magnification.

FIG. 13 represents a picture of a sample of myometrium tissue that was prepared with the use of an aqueous composition according to the present invention, the picture taken at 400× magnification.

FIG. 14 represents a comparison of the tissue samples of FIGS. 12 and 13.

FIG. 15 represents a picture of a sample of prostate tissue that was prepared without the use of an aqueous composition according to the present invention, the picture taken at 40× magnification.

FIG. 16 represents a picture of a sample of prostate tissue that was prepared with the use of an aqueous composition according to the present invention, the picture taken at 40× magnification.

FIG. 17 represents a picture of a sample of prostate tissue that was prepared without the use of an aqueous composition according to the present invention, the picture taken at 100× magnification.

FIG. 18 represents a picture of a sample of prostate tissue that was prepared with the use of an aqueous composition according to the present invention, the picture taken at 100× magnification.

FIG. 19 represents a picture of a sample of prostate tissue that was prepared without the use of an aqueous composition according to the present invention, the picture taken at 400× magnification.

FIG. 20 represents a picture of a sample of prostate tissue that was prepared with the use of an aqueous composition according to the present invention, the picture taken at 400× magnification.

FIG. 21 represents a picture of a sample of tonsil tissue that was prepared without the use of an aqueous composition according to the present invention, the picture taken at 40× magnification.

FIG. 22 represents a picture of a sample of tonsil tissue that was prepared with the use of an aqueous composition according to the present invention, the picture taken at 40× magnification.

FIG. 23 represents a picture of a sample of tonsil tissue that was prepared without the use of an aqueous composition according to the present invention, the picture taken at 100× magnification.

FIG. 24 represents a picture of a sample of tonsil tissue that was prepared with the use of an aqueous composition according to the present invention, the picture taken at 100× magnification.

FIG. 25 represents a picture of a sample of tonsil tissue that was prepared without the use of an aqueous composition according to the present invention, the picture taken at 400× magnification.

FIG. 26 represents another view of a sample of tonsil tissue that was prepared without the use of an aqueous composition according to the present invention, the picture taken at 400× magnification.

FIG. 27 represents a picture of a sample of tonsil tissue that was prepared with the use of an aqueous composition according to the present invention, the picture taken at 400× magnification.

FIG. 28 represents a picture of a sample of hernia sac tissue that was prepared without the use of an aqueous composition according to the present invention, the picture taken at 40× magnification.

FIG. 29 represents a picture of a sample of hernia sac tissue that was prepared with the use of an aqueous composition according to the present invention, the picture taken at 40× magnification.

FIG. 30 represents a picture of a sample of hernia sac tissue that was prepared without the use of an aqueous composition according to the present invention, the picture taken at 100× magnification.

FIG. 31 represents a picture of a sample of hernia sac tissue that was prepared with the use of an aqueous composition according to the present invention, the picture taken at 100× magnification.

FIG. 32 represents a picture of a sample of hernia sac tissue that was prepared without the use of an aqueous composition according to the present invention, the picture taken at 400× magnification.

FIG. 33 represents a picture of a sample of hernia sac tissue that was prepared with the use of an aqueous composition according to the present invention, the picture taken at 400× magnification.

FIG. 34 represents a picture of a sample of gallbladder tissue that was prepared without the use of an aqueous composition according to the present invention, the picture taken at 40× magnification.

FIG. 35 represents a picture of a sample of gallbladder tissue that was prepared with the use of an aqueous composition according to the present invention, the picture taken at 40× magnification.

FIG. 36 represents a picture of a sample of gallbladder tissue that was prepared without the use of an aqueous composition according to the present invention, the picture taken at 100× magnification.

FIG. 37 represents a picture of a sample of gallbladder tissue that was prepared with the use of an aqueous composition according to the present invention, the picture taken at 100× magnification.

FIG. 38 represents a picture of a sample of gallbladder tissue that was prepared without the use of an aqueous composition according to the present invention, the picture taken at 400× magnification.

FIG. 39 represents a picture of a sample of gallbladder tissue that was prepared with the use of an aqueous composition according to the present invention, the picture taken at 400× magnification.

DETAILED DESCRIPTION OF THE INVENTION

Unless indicated otherwise, indefinite articles such as "a" and "an" can refer to one species or more than one species. For example, the term "an alcohol" can refer to one alcohol or a mixture of at least two alcohols. Further, unless indicated otherwise, use of the definite article "the" does not limit a term to a single species. For example, the term "the alcohol" can refer to one alcohol or a mixture of at least two alcohols.

Unless indicated otherwise, temperatures reported herein are given in degrees centigrade.

Unless indicated otherwise, ranges defined by a minimum and/or maximum value include all real numbers within the range and include the minimum and/or maximum value defining the range.

One embodiment of the present invention relates to an aqueous solution that comprises:

(A) an organic polyol having from 2 to 20 carbon atoms and having a flash point of at least 93° C.;
(B) a base;
(C) a surfactant; and
(D) water, wherein the aqueous solution does not include an organic solvent having a flash point below 23° C. and a boiling point of at least 38° C.

Component (A)

Component (A) is an organic polyol having from 2 to 20 carbon atoms. As used herein, the term "organic polyol" refers to compounds having at least two OH-groups chemically bonded to atoms of the organic polyol, such as carbon atoms, and the flash point for each organic polyol in the scope of this invention is at least 93° C.

Non-limiting examples of component (A) are glycerin, pentaerythritol, ethylene glycol, and sucrose. Examples of component (A) may also include, but are not limited to glycerol, diglycerol, propylene glycol, sorbitol, pentylene glycol, trimethylolpropane, ditrimethylolethane, dipentaerythritol, pentaerythritol, alkoxylated pentaerythritol, trimethylolethane, trimethylolpropane, alkoxylated trimethylolpropane, dimethylolpropane, 1,3-dioxane-5,5-dimethanol, maltitol, xylitol, erythritol, isomalt, propanediol, butanediol, butanetriol, pentanediol, cyclohexanediol, dexapanthenol, pinanediol, decanediol, dodecanediol, hydrobenzoin, and sclareol. The organic polyols may also include polyethers or polyesters, such as polyethylene glycol, polypropylene glycol, and poly(tetramethylene ether) glycol.

Component (A) is not limited to only one species. Two or more organic polyols can be present in the aqueous solutions, provided that the flash point of the mixture is at least 93° C.

The amount of Component (A) in the aqueous solution is not particularly limited so long that it is present in sufficient amounts for the aqueous solution to soften tissue samples. In preferred embodiments, Component (A) is present in the aqueous solution in an amount of from 0.1 to 20% by volume of the total volume of the aqueous solution.

Component (B)

Component (B) is a base. As used herein, the term "base" preferably refers to compounds that are able to accept a proton, which can be explained by Brønsted-Lowry acid/base theory. Non-limiting examples of the base include ammonium hydroxide, hydroxides of alkali metals such as lithium hydroxide, sodium hydroxide, potassium hydroxide, rubidium hydroxide, and cesium hydroxide; hydroxides of alkaline earth metals such as beryllium hydroxide, magnesium hydroxide, calcium hydroxide, strontium hydroxide, and barium hydroxide.

Further, the base is not limited to only one species being present in the aqueous solutions; two or more species of base can be present in the aqueous solutions.

The amount of Component (B) in the aqueous solution is not particularly limited so long that it is present in sufficient amounts for the aqueous solution to soften tissue samples. In preferred embodiments, Component (B) is present in the aqueous solution in an amount of from 0.1 to 20% by volume of the total volume of the aqueous solution.

Component (C)

Component (C) is a surfactant. Examples of surfactant include, but are not limited to: anionic surfactants, cationic surfactants, non-ionic surfactants and zwitterionic surfactants.

Anionic surfactants include carboxylate salts, sulfonate salts, sulfate ester salts, and phosphate ester salts: carboxylate salts including soaps, N-acylamino acid salts, polyoxyethylene or polyoxypropylene alkylether carboxylate salts, and acylated peptides; sulfonate salts including alkylsulfonate salts, alkylbenzene and alkylnaphthalene sulfonate salts, naphthalene sulfonate salts, sulfosuccinate salts, a-olefin sulfonate salts, and N-acyl sulfonate salts; sulfate ester salts including sulfated oils, alkyl sulfate salts, alkylether sulfate salts, polyoxyethylene or polyoxypropylene alkylallylether sulfate salts, and alkylamide sulfate salts; and phosphate ester salts including alkylphosphate salts and polyoxyethylene or polyoxypropylene alkylallylether phosphate salts.

Cationic surfactants include aliphatic amine salts, aliphatic quaternary ammonium salts, benzalkonium chloride salt, benzethonium chloride, pyridinium salts, and imidazolinium salts; and amphoteric surfactants include carboxybetaine-type, sulfobetaine type, aminocarboxylate salts, imidazolinium betaines, lecithins, and alkylamine oxides.

Nonionic surfactants include ether-type, ether ester type, ester-type, nitrogen-containing-type; ether-type surfactants including polyoxyethylene alkyl and alkylphenylethers, alkyl allyl formaldehyde-condensed polyoxyethylene ethers, polyoxyethylene polyoxypropylene block polymer, and polyoxyethylene polyoxypropylene alkylethers; ether ester-type surfactants including glycerin ester polyoxyethylene ether, sorbitan ester polyoxyethylene ether, and sorbitol ester polyoxyethylene ether; ester-type surfactants including polyethylene glycol fatty acid esters, glycerin esters, polyglycerin esters, sorbitan esters, propylene glycol esters, and sucrose esters; nitrogen-containing surfactants including fatty acid alkanol amides, polyoxyethylene fatty acid amides, and polyoxyethylene alkyl amides; and the like.

Examples of other surfactants include esters such as glycerin esters, sorbitan esters, methoxy-acetic acid, ethoxy-acetic acid, 3-ethoxy-propionic acid and alanine ethyl ester; ethers such as polyethylene glycol, polypropylene glycol, polytetramethylene glycol, polyethylene glycol alkyl ethers, polyethylene glycol alkenyl ethers, alkyl polyethylene glycols, alkyl polyethylene glycol alkyl ethers, alkyl polyethylene glycol alkenyl ethers, alkenyl polyethylene glycols, alkenyl polyethylene glycol alkyl ethers, alkenyl polyethylene glycol alkenyl ethers, polypropylene glycol alkyl ethers, polypropylene glycol alkenyl ethers, alkyl polypropylene glycols, alkyl polypropylene glycol alkyl ethers, alkyl polypropylene glycol alkenyl ethers, alkenyl polypropylene glycols, alkenyl polypropylene glycol alkyl ethers and alkenyl polypropylene glycol alkenyl ethers; polysaccharides such as alginic acid, pectic acid, carboxymethyl cellulose, curdlan and pullulan; amino acid salts such as ammonium salt of glycine and sodium salt of glycine; polycarboxylic acids and salts thereof such as polyaspartic acid, polyglutamic acid, polylysine, polymalic acid, polymethacrylic acid, ammonium salt of polymethacrylic acid, sodium salt of polymethacrylic acid, polyamide acids, polymaleic acid, polyitaconic acid, polyfumaric acid, poly(p-styrene carboxylic acid), polyacrylic acid, polyacrylamide, amino polyacrylamide, ammonium salt of polyacrylic acid, sodium salt of polyacrylic acid, polyamido acid, ammonium salt of polyamido acid, sodium salt of polyamido acid and polyglyoxylic acid; vinylic polymers such as polyvinyl alcohol, polyvinyl pyrrolidone and polyacrolein; sulfonic acids and salts thereof such as ammonium salt of methyl taurine acid, sodium salt of methyl taurine acid, sodium salt of methyl sulfate, ammonium salt of ethyl sulfate, ammonium salt of butyl sulfate, sodium salt of vinyl sulfonate, sodium salt of 1-allyl sulfonate, sodium salt of 2-allyl sulfonate, sodium salt of methoxy-methyl sulfonate, ammonium salt of ethoxy-methyl sulfonate, sodium salt of 3-ethoxy-propyl sulfonate, sodium salt of methoxy-methyl sulfonate, ammonium salt of ethoxy-methyl sulfonate, sodium salt of 3-ethoxy-propyl sulfonate and sodium sulfo-succinate; and amides such as propionamide, acrylamide, methyl urea, nicotinamide, succinic acid amide and sulfanilamide.

A non-limiting example of a surfactant is a liquid detergent. As used herein, the term "liquid detergent" relates to surfactant in liquid form combined with builders and other excipients customary in detergents. The components of the liquid detergent are not particularly limited, so long as the liquid detergent does not include a component that has a flash point below 23° C. and a boiling point of at least 38° C.

Examples of liquid detergents include industrial detergents, household detergents, and commercial detergents. The commercial detergents may include the household and industrial detergents.

Examples of household detergents include ANNETTE'S PERFECT CLEANSER COMPANY, ARIEL, BARF SOAP, BIZ, BOLD, BREEZE, CHEER, COLD POWER, COLOUR CATCHER, DASH, DAZ, DIDI SEVEN, DREFT, FRESH START, GAIN, GHARI, LUVIL, NIRMA, OXYDOL, PERSIL, PERSIL POWER, PUREX, RINSO, SUNLIGHT, SURF, SURF EXCEL, TIDE, TOLYPERS, WHEEL, WIN, WISK, WOOLITE, RUBY MOON, CHARLIE'S SOAP, MOUNTAIN GREEN, MOLLIE'S SUDS, HONEST COMPANY, ALL, COUNTRY SAVE, DREFT, DROPPS, ECOS, GAIN, IVORY, KIRKLAND'S, MELALEUCA, METHOD, NATURE CLEAN, PENGUIN, OXYPRIME, PLANET, PUREX, AND VASCA.

Examples of industrial detergents include CHAPS, CHAPSO, NDSB-256, NONIDET P40, VANABAN, VANABAN R, BANASOL, CORRONOL H, CORRONOL 12, OXYBAN E3, CORROSOLGRAS, CORRONET, CORROBOPIN, CORROLAV, CORROSAIN, CARBAN PLUS 3 AND SUPER CARBAN.

The amount of Component (C) in the aqueous solution is not particularly limited so long that it is present in sufficient amounts for the aqueous solution to soften tissue samples. In preferred embodiments, Component (C) is present in the aqueous solution in an amount of from 0.1 to 20% by volume of the total volume of the aqueous solution.

Component (D)

Water is present in the aqueous solutions as component (D), and the amount is not particularly limited so long that it is present in amounts for the other components to be present in the amounts described herein.

Flammable Organic Solvents

The aqueous solutions of this embodiment do not contain or include organic solvents, meaning any amount of the organic solvent, if any does not exceed the detection limit of the organic solvent. As used herein, the term "organic solvent" relates to carbon-containing compounds that are in liquid form at standard temperature and pressure and have a flash point below 23° C. and a boiling point of at least 38° C.

Non-limiting examples of the organic solvent include: aliphatic alcohols such as methanol, ethanol, propanol (n- and iso-), and butanol (n-, tert-), where the OH group is present on any carbon atom of ethanol, propanol, and butanol; ketones such as acetone, methyl ethyl ketone; aliphatic liquid organic solvents such as pentane, hexane, heptane, octane, nonane, and mixtures thereof; halogenated organic solvents such as methylene chloride, chloroform, carbon tetrachloride, chlorobenzene; ethers such as ethyl ether, tetrahydrofuran, methyl t-butyl ether; and esters such as ethyl acetate.

In particularly preferred embodiments, the aqueous solutions do not contain any of methanol, ethanol, propanol, and butanol, either the absolute absence of these solvents or in an amount below the detection limit of these solvents.

In the most preferred embodiments, the aqueous solution does not contain methanol, either the absolute absence of these solvents or in an amount below the detection limit of these solvents.

Other Components

The aqueous solutions of the present invention can comprise additional, unrecited components. For example, the aqueous solution may further comprise an additive, a tackifier, a coloring agent, a dye, a retarder, a fluid loss agent, a friction reducing agent, an expanding agent, and a dispersant.

In the embodiment where the aqueous solution contains a coloring agent or dye, the coloring agent and/or dye can preferably be added to the solution such that the soak solution that softens the paraffin blocks is a certain color that is visible to the naked eye.

pH of the Aqueous Solutions

In preferred embodiments of this invention, the aqueous compositions that comprise components (A) through (D) have a pH value that gives the aqueous composition a basic character. For example, the pH can be from greater than 7 to 14, preferably from greater than 7 to 12, most preferably from 8 to 11.

The end points above are values measured within ±0.1. Further, the pH of the aqueous compositions can be optimized through routine experimentation to produce an aqueous composition that has a pH suitable for histotechnologic studies.

Additional Embodiments

In some embodiments of the invention, the aqueous solutions consist essentially of: (A) an organic polyol having from 2 to 20 carbon atoms and having a flash point of at least 93° C.; (B) a base; (C) a surfactant; and (D) water, wherein the aqueous solution does not include an organic solvent having a flash point below 23° C. and a boiling point of at least 38° C., and other additional components that do not materially affect the basic and novel characteristics of the aqueous solutions of the present invention.

In other embodiments of the invention, the aqueous solutions consist: (A) an organic polyol having from 2 to 20 carbon atoms and having a flash point of at least 93° C.; (B) a base; (C) a surfactant; and (D) water, wherein the aqueous solution does not include an organic solvent having a flash point below 23° C. and a boiling point of at least 38° C.

Methods of Making the Aqueous Solutions According to the Present Invention

Another embodiment of the present invention relates to methods of making the aqueous solutions of the present invention. These methods comprise:

mixing components (A), (B), (C), and (D) in a container at a temperature and pressure sufficient to obtain an aqueous solution according to the present invention.

Non-limiting methods for mixing components (A), (B), (C), and (D) include stirring the components in the container, shaking the container, and using a magnetic stirrer in the container and applying a magnetic field to the magnetic stirrer.

The temperature and pressure during the mixing stage is not particularly limited, so long as the mixing takes place and the components do not condense into a solid or evaporate out solution. Preferably, the temperature is room temperature and the pressure is atmospheric pressure.

Methods of Using the Aqueous Solutions According to the Present Invention

Another embodiment of the present invention relates to methods of using the aqueous solutions described above as a soaking solution for producing tissue samples for histopathologic review. The tissue sample is not particularly limited. Non-limiting examples include all human and animal (vertebrae) biologic tissues in solid and liquid form, applications in natural sciences, such as plants and invertebrate zoology, and artificial and prosthetic material studies for tissue sectioning with artificial materials such as Bio-Oss collagen, which is used for matrix for bone implants.

In preferred embodiments, the method comprises placing a tissue sample on a surface, pouring enough of an aqueous solution according to the present invention over the tissue sample to soak the tissue sample, and allowing the tissue sample to soak in the aqueous solution. Examples of the surface on which the tissue sample can be present include, but are not limited to, a paraffin block, an ice tray, and a cooling tray. The time for soaking is not particularly limited, provided that the tissue sample does not swell. Preferably, the time for soaking is from 1 to 5 minutes, most preferably from 3 to 5 minutes.

Thereafter, the soaked tissue sample is, e.g., cut into desired sections having a size suitable for histopathologic studies. In a non-limiting example, the soaked tissue sample is cut into 5 micron sections. Cutting can take place with any instrument suitable for preparing tissue samples for histopathologic studies.

Histologic sample preparation (in humans/animals) utilizes tissue specimens for sectioning, staining and diagnosis. The standard paraffin process (tissue processing) moves specimens through a series of stages so the soft tissue is supported in a medium that allows histologic sectioning. Tissue is grossly examined by a trained prosector (pathologist/researcher/pathology assistant) and areas of interest are selected for histopathologic examination.

The standard/basic steps in tissue processing are:
(i) fixation;
(ii) tissue processing; and
(iii) tissue embedding.

Fixation is commonly performed with formalin. However, fixation is not limited to use of formalin, and may be performed with alternative tissue fixatives that preserves the tissue, such as alcohol. The length of fixation may alter quality of the tissue sample.

Tissue processing is carried out by automated instruments that treat the fixed tissue through a series of successive dehydrations, and clear and ultimately infiltrate the tissue with paraffin wax. The length/time of tissue processing may be altered depending on size of the tissue. For example, smaller tissues may require about 6 hours of tissue processing in a "short run" and larger tissue sections, such as standard tissues sections, may require from 9 to 10 hours of tissue processing, all depending on the various instruments used for processing.

Tissue embedding is a step the occurs after tissue processing that allows orientation of the specimen in a paraffin block that can be sectioned and is easy to store, handle and ship to other laboratories for further studies (i.e. molecular studies in cancer diagnoses or second opinions). Tissue sectioning is performed with a microtome to produce very thin sections (typically 4 to 5 microns), which are placed on a microscope slide and subjected to a staining method. Standard histology stains include, for example, hematoxylin and eosin, but alternatives such as Periodic Acid Schiff (PAS) stains can also be used as a pantheon of special histochemical stains, immunohistochemical stains as well as molecular studies such as fluorescence in-situ hybridization (FISH) or other molecular studies.

EXAMPLES

Examples of inventive and comparative softening solutions are provided herein, and the scope of the present invention is not limited by the examples.

The samples displayed in FIGS. 1-39 were viewed under a microscope at magnifications of 40×, 100×, and 400×. The microscope used to capture the images of these figures was a Olympus Vanox AHBS3 AH-3 microscope with an Olympus DP70 Camera attachment.

Example 1

Five milliliters of glycerin, five milliliters of liquid soap, and five milliliters of ammonium hydroxide were added to a 100 milliliter graduated cylinder. Thereafter, 85 milliliters of water was added to the graduated cylinder to prepare an aqueous solution.

Example 2 (Comparative)

Endometrium tissue was obtained and cut to an appropriate size for use as a sample. A tissue softening composition was not used prior to cutting. FIG. 1 shows the form of the tissue sample post cutting, where a large dark spot representing a rolled tissue portion was observed in the lower left-hand section of the tissue sample. The tissue sample was viewed at 40× magnification.

Example 3 (Inventive)

Endometrium tissue was obtained as in Example 2 and cut to an appropriate size for use as a sample. Unlike in Example 2, the aqueous composition of Example 1 was used as a tissue softener prior to cutting the tissue. FIG. 2 shows the form of the tissue sample post cutting, and, as a result of using the aqueous composition according to Example 1, the tissue did not exhibit the sample defect as in Example 2. Further, a well-defined tissue sample was obtained, showing the various histologic tissue structures within the tissue sample with clarity. The difference in the results between Examples 2 and 3 is further seen in FIG. 3, which shows a side-by-side comparison of the tissue samples of Examples 2 and 3.

Example 4 (Comparative)

The same endometrium tissue sample of Example 2 was viewed at 100× magnification, and this view reveals damage to intra-epithelial damage to epithelium tissue. This view is seen in FIG. 4.

Example 5 (Inventive)

The same endometrium tissue sample of Example 3 was viewed at 100× magnification, and, unlike in Example 4, this view reveals far less intra-epithelial damage to epithelium tissue within the sample. Further, smaller glands within the tissue were better preserved than in Example 4. This view is seen in FIG. 5.

Example 6

FIGS. 6 and 7 show the same endometrium tissue samples of Examples 2 and 3, respectively, but each viewed at 400× magnification. Nuclear features within the tissue sample of Example 3, i.e. the one soaked in the aqueous solution of Example 1, were more visible than in the tissue sample of Example 2, i.e., the one prepared without a tissue softener.

Example 7 (Comparative)

Myometrium tissue was obtained and cut to an appropriate size for use as a sample. A tissue softening composition was not used prior to cutting. FIG. 8 shows the form of the tissue sample post cutting at 40× magnification, where a large line runs through the left-hand side of the tissue sample. This line represents a damaged section of tissue from the knife used to cut the tissue sample. FIGS. 10 and 12 show the same tissue sample at 100× and 400× magnification, respectively, where the tissue damage from the knife blade is seen at an amplified level.

Example 8 (Inventive)

Myometrium tissue was obtained as in Example 7 and cut to an appropriate size for use as a sample. Unlike in Example 7, the aqueous composition of Example 1 was used as a tissue softener prior to cutting the tissue. FIG. 9 shows the form of the tissue sample post cutting, and, as a result of using the aqueous composition according to Example 1, the tissue did not exhibit the sample defect as in Example 7. FIGS. 11 and 13 show the same tissue sample at 100× and 400× magnification, respectively, where the various histologic tissue structures within the tissue sample are seen clearly and little-to-no damage is seen from the knife blade.

FIG. 14 shows the 400× magnified views of the tissue samples of FIGS. 12 and 13, respectively, and the knife damage is clearly seen in this side-by-side comparison. This comparison highlights the effect of the aqueous composition according to Example 1 and its ability to promote excellent and clean samples for histological studies.

Example 9 (Comparative)

Prostate tissue was obtained and cut to an appropriate size for use as a sample. A tissue softening composition was not used prior to cutting. FIG. 15 shows the form of the tissue sample post cutting at 40× magnification, where a fold in the tissue sample resulted during processing of the tissue sample without a tissue softener composition. The fold obscured structural features of the tissue sample, particularly small biopsies and core biopsies.

FIGS. 17 and 19 show the tissue sample of this comparative example at 100× and 400× magnification, respectively. The magnitude of the fold is enhanced in these figures, and the effect of the fold on obscuring the small biopsies and core biopsies is readily seen.

Example 10 (Inventive)

Prostate tissue was obtained as in Example 9 and cut to an appropriate size for use as a sample. Unlike in Example 9, the aqueous composition of Example 1 was used as a tissue softener prior to cutting the tissue. FIG. 16 shows the form of the tissue sample post cutting, and, as a result of using the aqueous composition according to Example 1, the tissue did not exhibit the sample fold as in Example 9. The smaller biopsies and core biopsies were more visible compared to the tissue sample of Example 9.

FIGS. 18 and 20 show the tissue sample of this comparative example at 100× and 400× magnification, respectively. The small biopsies and core biopsies are seen with increased clarity compared to the prostate tissue sample obtained without the use of a tissue softener.

Example 11 (Comparative)

Tonsil tissue was obtained and cut to an appropriate size for use as a sample. A tissue softening composition was not used prior to cutting. FIG. 21 shows the form of the tissue sample post cutting at 40× magnification, where a fold in the tissue sample resulted during processing of the tissue sample without a tissue softener composition. In addition, a damaged section of the tissue resulted from the knife cutting the tissue. FIGS. 23, 25, and 26 show this tissue sample at 100× and 400× magnification, where the damage during cutting is more visible.

Example 12 (Inventive)

Tonsil tissue was obtained as in Example 11 and cut to an appropriate size for use as a sample. Unlike in Example 11, the aqueous composition of Example 1 was used as a tissue softener prior to cutting the tissue. FIG. 22 shows the form of the tissue sample post cutting, at 40× magnification, and, as a result of using the aqueous composition according to Example 1, the tissue sample was not damaged during cutting.

FIGS. 24 and 27 show the same tissue sample at 100× and 400× magnification. Unobstructed views of histologic tissue structures within the tonsil tissue resulted from the use of the aqueous composition of Example 1.

Example 13 (Comparative)

Hernia sac tissue was obtained and cut to an appropriate size for use as a sample. A tissue softening composition was not used prior to cutting. FIG. 28 shows the form of the tissue sample post cutting at 40× magnification, where a tissue shatter and a tissue artifact from the knife rolling through the sample resulted during processing of the tissue sample without a tissue softener composition. FIGS. 30 and 32 show this tissue sample at 100× and 400× magnification, where the damage during cutting is more visible.

Example 14 (Inventive)

Hernia sac tissue was obtained as in Example 13 and cut to an appropriate size for use as a sample. Unlike in Example 13, the aqueous composition of Example 1 was used as a tissue softener prior to cutting the tissue. FIG. 29 shows the form of the tissue sample post cutting, at 40× magnification, and, as a result of using the aqueous composition according to Example 1, the tissue sample was not damaged during cutting.

FIGS. 31 and 33 show the same tissue sample at 100× and 400× magnification. Unobstructed views of histologic tissue structures within the tonsil tissue resulted from the use of the aqueous composition of Example 1.

Example 15 (Comparative)

Gallbladder tissue was obtained and cut to an appropriate size for use as a sample. A tissue softening composition was not used prior to cutting. FIG. 34 shows the form of the tissue sample post cutting at 40× magnification, where a tissue shatter is visible in the tissue sample. FIGS. 36 and 38 show this tissue sample at 100× and 400× magnification, where the tissue shatter is more visible.

Example 16 (Inventive)

Gallbladder tissue was obtained as in Example 15 and cut to an appropriate size for use as a sample. Unlike in Example 15, the aqueous composition of Example 1 was used as a tissue softener prior to cutting the tissue. FIG. 35 shows the form of the tissue sample post cutting, at 40× magnification, and, as a result of using the aqueous composition according to Example 1, the tissue sample was not damaged during cutting.

FIGS. 37 and 39 show the same tissue sample at 100× and 400× magnification. Unobstructed views of histologic tissue structures within the tonsil tissue resulted from the use of the aqueous composition of Example 1.

We claim:

1. An aqueous solution that comprises:
   (A) an organic polyol having from 2 to 20 carbon atoms and having a flash point of at least 93° C.;
   (B) a base;
   (C) a surfactant; and
   (D) water, present in an amount sufficient so that components (A), (B), and (C) are present in the form of a fluid aqueous solution at room temperature,
   wherein the aqueous solution does not include an organic solvent having a flash point below 23° C. and a boiling point of at least 38° C.,
   wherein component (A) is selected from the group consisting of glycerin, pentaerythritol, ethylene glycol, sucrose, glycerol, diglycerol, sorbitol, pentylene glycol, trimethylolpropane, ditrimethylolethane, dipentaerythritol, pentaerythritol, alkoxylated pentaerythritol, trimethylolethane, trimethylolpropane, alkoxylated trimethylolpropane, dimethylolpropane, 1,3-dioxane-5,5-diethanol, maltitol, xylitol, erythritol, isomalt, propanediol, butanediol, butanetriol, pentanediol, cyclohexanediol, dexapanthenol, pinanediol, decanediol, dodecanediol, hydrobenzoin, sclareol, and a combination thereof,
   wherein propylene glycol is not present in the aqueous composition, and
   wherein the aqueous composition has a pH of from 7.1 to 14.

2. The aqueous solution according to claim 1, wherein component (A) further comprises at least one polyether or polyester.

3. The aqueous solution according to claim 2, wherein the polyether or polyester comprises polyethylene glycol, polypropylene glycol, poly(tetramethylene ether) glycol, or a mixture thereof.

4. The aqueous solution according to claim 1, wherein component (A) is present in an amount of from 0.1 to 20% by volume of the total volume of the aqueous solution.

5. The aqueous solution according to claim 1, wherein component (B) comprises ammonium hydroxide, a hydroxide of an alkali metal, a hydroxide of an alkaline earth metal, or a combination thereof.

6. The aqueous solution according to claim 1, wherein component (B) comprises ammonium hydroxide, lithium hydroxide, sodium hydroxide, potassium hydroxide, rubidium hydroxide, cesium hydroxide, beryllium hydroxide, magnesium hydroxide, calcium hydroxide, strontium hydroxide, barium hydroxide, or a combination thereof.

7. The aqueous solution according to claim 1, wherein component (B) is present in an amount of from 0.1 to 20% by volume of the total volume of the aqueous solution.

8. The aqueous solution according to claim 1, wherein component (C) comprises an anionic surfactant, a cationic surfactant, a non-ionic surfactant, a zwitterionic surfactant, or a combination thereof.

9. The aqueous solution according to claim 1, wherein component (C) is in the form of a liquid detergent, which comprises a surfactant in liquid form combined with a builder and an excipient present in liquid detergent, where the liquid detergent does not include a component that has a flash point below 23° C. and a boiling point of at least 38° C.

10. The aqueous solution according to claim 1, wherein component (C) is present in an amount of from 0.1 to 20% by volume of the total volume of the aqueous solution.

11. The aqueous solution according to claim 1, which does not include at least any of methanol, ethanol, propanol, and butanol.

12. The aqueous solution according to claim 1, which has a pH of from 8 to 12.

13. The aqueous solution according to claim 1, which has a pH of from 8 to 11.

14. A method of making the aqueous solution according to claim 1, the methods comprising:
    mixing components (A), (B), (C), and (D) in a container at a temperature and pressure sufficient to obtain the aqueous solution.

15. The method according to claim 14, wherein said mixing is carried out by stirring the components in the container, shaking the container, using a magnetic stirrer in the container and applying a magnetic field to the magnetic stirrer, or a combination thereof; and
    the temperature is room temperature and the pressure is atmospheric pressure.

16. A method of using the aqueous solution according to claim 1, which comprises:
    soaking a tissue sample with the aqueous solution for a time period sufficient to soak the tissue sample but not swell the tissue sample; and
    cutting the soaked tissue sample into sections suitable for histopathologic studies.

17. The method according to claim 16, wherein said soaking is carried out for a period of from 1 to 5 minutes.

18. The method according to claim 16, for the use of tissue fixation; tissue processing; and tissue embedding during histopathologic studies of the tissue.

19. The aqueous solution according to claim 1, wherein
    component (A) is glycerin, present in an amount of from 0.1 to 5 vol %, relative to 100 vol % of the aqueous solution,
    component (B) is ammonium hydroxide, present in an amount of 0.1 to 5 vol %, relative to 100 vol % of the aqueous solution,
    component (C) is liquid soap, present in an amount of 0.1 to 5 vol %, relative to 100 vol % of the aqueous solution.

* * * * *